(12) United States Patent
Appel et al.

(10) Patent No.: US 7,301,060 B2
(45) Date of Patent: *Nov. 27, 2007

(54) PROCESS FOR CONVERSION OF ORGANIC, WASTE, OR LOW-VALUE MATERIALS INTO USEFUL PRODUCTS

(75) Inventors: Brian S. Appel, West Hempstead, NY (US); James H. Freiss, Stony Brook, NY (US); William F. Lange, Wilmette, IL (US)

(73) Assignee: AB-CWT, LLC, West Hempstead, NY (US)

( * ) Notice: Subject to any disclaimer, the term of this patent is extended or adjusted under 35 U.S.C. 154(b) by 205 days.

This patent is subject to a terminal disclaimer.

(21) Appl. No.: 10/957,540

(22) Filed: Sep. 30, 2004

(65) Prior Publication Data

US 2006/0004237 A1 Jan. 5, 2006

Related U.S. Application Data

(63) Continuation-in-part of application No. 10/717,076, filed on Nov. 18, 2003.

(60) Provisional application No. 60/458,520, filed on Mar. 28, 2003.

(51) Int. Cl.
*C07C 1/20* (2006.01)
(52) U.S. Cl. ...................... 585/240; 585/241
(58) Field of Classification Search ............... 585/240, 585/241
See application file for complete search history.

(56) References Cited

U.S. PATENT DOCUMENTS

| | | | |
|---|---|---|---|
| 4,192,734 A | 3/1980 | Pavlica et al. | |
| 5,269,947 A | 12/1993 | Baskis | |
| 5,360,553 A | 11/1994 | Baskis | |
| 5,543,061 A | 8/1996 | Baskis | |
| 2003/0153797 A1 | 8/2003 | Percell | |

OTHER PUBLICATIONS

Third Party Submission under 37 C.F.R. § 1.99 submitted by Paul Baskis., Dec. 30, 2001.

*Primary Examiner*—Tam M. Nguyen
(74) *Attorney, Agent, or Firm*—Morgan Lewis & Bockius LLP

(57) ABSTRACT

The present invention addresses the processing of waste and low-value products to produce useful materials in reliable purities and compositions, at acceptable cost, and with high energy efficiency. In particular, the invention comprises a multi-stage process that converts various feedstocks such as offal, animal manures, municipal sewage sludge, that otherwise have little commercial value, to useful materials including gas, oil, specialty chemicals, and carbon solids. The process subjects the feedstock to heat and pressure in a reducing environment accomplished by controlled addition of sulfur and sodium, separates out various components, then further applies heat and pressure to one or more of those components. The invention further comprises an apparatus for performing a multi-stage process of converting waste products into useful materials, and at least one oil product that arises from the process.

33 Claims, 10 Drawing Sheets

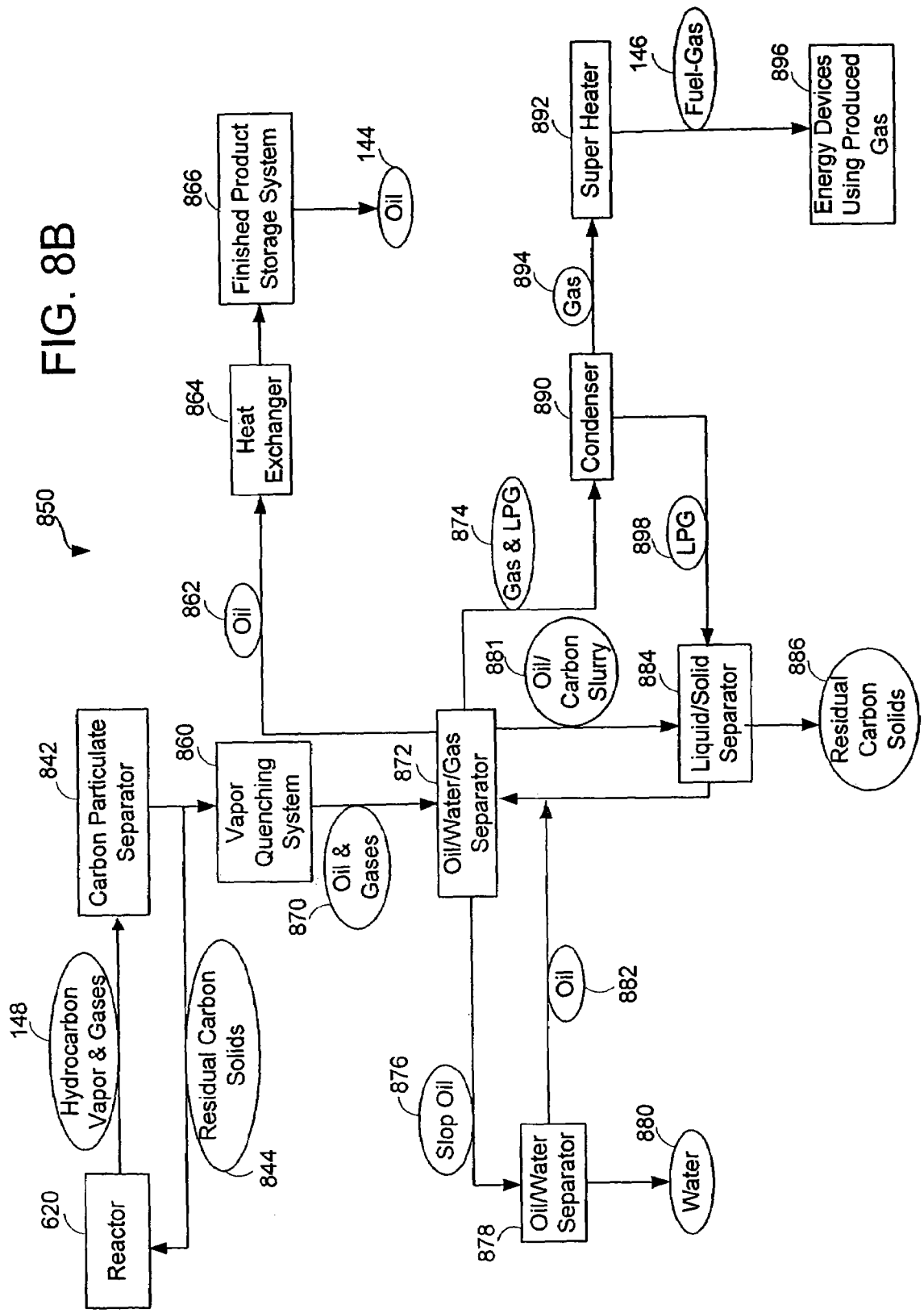

PROCESS FOR CONVERSION OF ORGANIC, WASTE, OR LOW-VALUE MATERIALS INTO USEFUL PRODUCTS

CLAIM OF PRIORITY

This application is a continuation-in-part of U.S. patent application Ser. No. 10/717,076, filed Nov. 18, 2003, which in turn claims the benefit of priority under 35 U.S.C. § 119(e) to U.S. provisional application Ser. No. 60/458,520, filed Mar. 28, 2003, both of which are incorporated herein by reference in their entirety.

FIELD OF THE INVENTION

The present invention generally relates to the processing of waste or low-value products to form useful raw materials. More specifically, the invention relates to a process and apparatus for converting agricultural, and other waste or low-value materials that contain carbon-based compounds, to commercially useful products such as fuel oil, fertilizer and specialty organic chemicals. The invention reduces the environmental pollution potential arising from inorganic waste stream.

BACKGROUND

It has long been recognized that many of the waste products generated by human society can, ultimately, be broken down into a small number of simple organic materials that have their own intrinsic value. If this transformation could be achieved in an energy-efficient manner, and on a large enough scale, then there could be enormous benefits to society.

Most living materials, as well as most synthetic organic substances used in domestic and commercial applications comprise carbon-based polymers of various compositions. Under appropriate conditions, most such materials—including wood, coal, plastics, tires, and animal waste—will break down to a mixture of gaseous products, oils, and carbon. Materials such as agricultural waste products may also contain inorganic substances that break down to mineral products. Almost all of these products, whether organic or inorganic, can enjoy new lives in a host of beneficial and often lucrative applications.

Not only is the principle of creating useful materials from otherwise unserviceable waste appealing: recycling of waste materials is of fundamental importance to the way that the burgeoning human population will address major challenges in the $21^{st}$ century. Two principal challenges facing humanity are coping with a finite supply of the Earth's resources, and with curtailing the growing threat to the environment from global warming. Indeed, an idea that is rapidly gaining currency is that global warming could be mitigated by recycling carbon-based materials from within the biosphere rather than introducing new sources of carbon from underground deposits of oil, natural gas and coal.

As of today, however, industries that produce huge volumes of waste products comprising largely organic materials face enormous challenges in disposing and storing that waste, as well as putting it to maximum beneficial use.

A case in point, the food processing industry around the world generates billions of pounds of organically rich wastes per year. These wastes are associated with the processing of both animal and plant products, and include turkey-, fish-, chicken-, pig-, and cattle-processing and husbandry wastes. The food processing industry continues to grow and its members face significant economic and environmental pressures to do something productive with their waste products. Such waste products give rise to a number of critical problems. The generation of greenhouse gases such as carbon dioxide and methane by landfilling, land applying, or digesting food wastes, without any other benefit, is one such problem. Ideally, the food industry must adopt efficient and economical ways of managing their wastes without discharging odorous or objectionable pollutants.

More recently, the cost of warehousing unusable byproducts in many areas is growing in significance. The types of waste products that can be fed to agricultural livestock have become increasingly regulated. For example, in the wake of BSE/CJD scares in Europe, many waste products are simply being warehoused, pending a suitable fate. Clearly, there is an additional urgent need to find an acceptable means to cleanly process and utilize such materials. Preferably, a way to convert food-processing wastes into useful, high-value products needs to be found.

An additional drive to seek treatment alternatives is the combined enforcement of wastewater discharge regulations and the escalation of sewage surcharges. The food processing industry must seek cost-effective technologies to provide pretreatment or complete treatment of their wastewaters and solid (wet) wastes. Historically, food processing facilities located within or adjacent to municipalities, have relied on local publicly owned treatment works (POTWs) for wastewater treatment and disposal. Increasingly, this option is becoming less available, as a result of more rigorous enforcement. Pressure to comply with wastewater discharge permits has increased. Dwindling federal grants for construction of new and upgraded POTWs also means that this option is less appealing. Thus, the food-processing industry is increasingly being pressured with regard to how to effectively dispose of its inedible products.

Bioaccumulation of persistent chemicals such as dioxins and the potential for the spread of life threatening diseases such as Mad Cow Disease (BSE) is another threat to food processors and food consumers alike. This threat is greatly exacerbated by refeeding food processing residues to farm animals. The food processing industry needs economical solutions to break this cycle.

Furthermore, municipal and regional sewer authorities are requiring industries to reduce their organic biochemical oxygen demand (BOD), chemical oxygen demand (COD), and solid loading on the sewers. Due to the high BOD concentrations typically found in high-strength food process wastewaters with high levels of suspended solids, ammonia, and protein compounds, the food processing industry is under additional scrutiny. Food processing facilities need cost-effective and application-specific treatment technologies to manage their wastewaters and solid wastes effectively.

Similar problems are multiplied, magnified and augmented in many different ways across other industries. For example, the generation of malodorous air emissions associated with rendering plants—that convert animal waste by heat into fats and proteins, is one such problem. Another is land application of municipal biosolids that contain high concentrations of pathogens.

There have been various approaches developed to process used and waste tires—say from truck and passenger vehicles—into useful products including fuels, petroleum oils, carbon, fuel-gases, as well as feedstocks for manufacture of tires and other rubber products. Typically, these schemes involve heating and dissolving the tires in solvents. Some of the schemes attempt to devulcanize the tire rubber, i.e., break the sulfur bonds that connect the constituent polymers along their lengths. Others attempt to depolymerize the rubber material. Depolymerization breaks the long chain polymers into shorter ones that are more fluid so can more easily be used as a product such as a fuel oil. Some schemes involve the use of water under conditions near or above its critical point (~3,200 psi and ~370° C.) where water is a very good solvent for, and reactant with, the tire material. However, such schemes are energetically inefficient because of the energy required to achieve super-critical conditions. Furthermore, processing at super-critical conditions also requires expensive super-alloy operating equipment.

Aerobic and anaerobic digesters have been employed at sewage treatment plants to treat municipal sewage sludge. There are a number of problems associated with their use. The basic principle behind their operation is that biologically rich materials are directed into large holding vessels that contain bacteria which digest the biological materials. Typically, dissolved solids are directed to an aerobic digester, and suspended solids are directed to an anaerobic digester. Once the nutritional feed materials are exhausted, the bugs can no longer sustain themselves, and they die. The end-product of the digestion period is a sludge that contains the dead bacteria, and which must be disposed of in some way. One problem with the resulting material is that it still contains pathogens. Additional problems with the whole process, in general, include that the holding times in the digester vessels can be as long as 17 days, and that the operating conditions are difficult to maintain. For example, the relatively large vessel (typically 20-30 ft. in diameter) is usually maintained at above 85° F., and in some cases above 122° F.

All of the disposal technologies currently available to industries, in particular the food processing industry, have significant limitations and drawbacks that provide an incentive to search for alternative processes. This applies to technologies in addition to the use of existing POTWs. In particular, four types of approach, land disposal (landfills, composting, land application), biotreatment, traditional thermal oxidation treatments such as incineration/combustion, and pyrolysis/gasification, all have separate drawbacks.

Drawbacks for land disposal include: high haulage or transport costs, significant potential for groundwater contamination from leaching, and the exposure of area residents to high concentrations of hazardous pollutants (such as pathogens in the instance of land application). Landfills produce gas that can create air pollution concerns, including the generation of greenhouse gases.

Disadvantages for biotreatment of waste include difficulty with control, and inability to verify performance because of the difficulty with verifying adequate airflow into the soil. The airflow must be maintained to provide oxygen if using aerobic bacteria. For example, bacteria that may have been developed to consume specific compounds will, when placed in soil, activate alternative enzyme systems to consume the easiest available compounds.

Drawbacks with older units that carry out incineration or combustion include the requirement to add equipment to meet air pollution emission standards that are continually being made more stringent by the government. It may also take longer to obtain air discharge permits for incinerators than for other technologies due to significant community concerns about incineration. Additionally, the treatment of the waste at the exhaust means treating large volumes of gas so that very large plant equipment is required. The feedstock is also low in calorific value. Some incinerators are not compatible with solid fuels or solid waste, as these materials will start to oxidize too high up in the furnace. Conversely, high moisture content in the feedstocks is also a problem because during incineration or combustion the water is vaporized and removed—a process which requires approximately 1,000 Btu/lb of water vaporized. This represents huge heat/energy losses to the system.

The last category of technique employed—pyrolysis/gasification—is appealing because, unlike the others mentioned, it attempts to convert the waste into utilizable materials, such as oils and carbon. Of principal concern when searching for optimum ways of breaking down waste products is how to adjust the composition of the resulting materials while minimizing the amount of energy needed to effect the breakdown. In the past, the principal pyrolysis and gasification methods that have been employed attempted to break down the waste products in a single stage process, but a single stage has been found to offer inadequate control over purity and composition of the end products.

Pyrolyzers have been used to break down organic materials to gas, oils and tar, and carbonaceous materials. A pyrolyzer permits heating of the organic materials to high temperatures, ~400-500° C., but has poor energy efficiency and gives little control over the composition of the resulting materials. In particular, most waste products—especially those from the agricultural industry—contain up to 50% water. The pyrolyzer needs to boil off that water, a process that is very energetically demanding. Additionally, a pyrolysis chamber tends to be large in order to maximize throughput, but then gives rise to significant temperature gradients across the chamber. Thus, the pyrolysis process involves an uneven heating of the waste products and leads to poor quality or impure tars and oils in the resulting end products.

Gasifiers have been used to achieve a partial combustion of waste products. In essence, a gas—usually air, oxygen, or steam—is passed over the waste products in an amount that is insufficient to oxidize all the combustible material. Thus, some combustion products such as $CO_2$, $H_2O$, CO, $H_2$ and light hydrocarbons are produced, and the generated heat converts the remaining waste products into oils, gases, and carbonaceous material. The gases produced will contain some of the input gases, but any gases that are produced are too voluminous to be stored and must be used immediately or piped to a place where they can be utilized. Gasifiers also suffer from some of the same drawbacks as pyrolyzers: for example, a water-containing waste product will consume a lot of energy in vaporizing the water content.

Both pyrolysis and gasification methods additionally have the problem that the resulting materials contain unacceptable levels of impurities. In particular, sulfur- and chlorine-containing materials in the waste products give rise, respectively, to sulfur-containing compounds such as mercaptans, and organic chlorides in the resulting end products. Typically, chlorinated hydrocarbons at levels of 1-2 ppm can be tolerated in hydrocarbon oils, but neither gasification nor pyrolysis methods can guarantee such a low level with any reliability.

Furthermore, pyrolysis and gasification methods have low efficiencies, typically around 30%. One reason for this is that the products are not optimum in terms of calorific content. A further reason is that, in a single stage process, the materials are not produced in a form that easily permits their energy to be usefully re-used within the process. For example, it is difficult to capture the thermal energy in the solid products that are produced and redirect it to assist in the heating of the reaction vessel.

Overall, then, pyrolysis/gasification methods suffer in several ways. The oil product is generally rich in undesirable high viscosity components such as tar and asphalt. Both pyrolysis and gasification processes have poor heat transfer properties and consequently do not heat evenly. Therefore, end products vary greatly in number with few of sufficient quantity or quality for economical recovery. Wet feedstocks require significant energy to vaporize and represent large energy losses to the system since the water leaves as a gas in the stack. Thus, in summary, the disadvantages of pyrolysis/gasification are that the overall operating cost is high, the process is capital intensive and some by-products may have limited or no value.

Although there have been many variants of the pyrolysis and gasification methods, all of which have suffered from broadly similar drawbacks, systems that replace the single-stage process of the prior methods with a two-stage process—see, for example, U.S. Pat. Nos. 5,269,947, 5,360,553, and 5,543,061—have resulted in increases in processing efficiency. In a first stage (often referred to as the "wet" stage), the waste products are subjected to heat at around 200-250° C. and at about 20-120 atmospheres pressure. Under such conditions the water content of the waste material hydrolyzes many of the biopolymers that may be present such as fats and proteins to form a mixture of oils. In a second stage (often called the "dry" stage), the mixture is flashed down to low pressure, during which around half of the water is driven off as steam. The mixture is heated still further to evaporate off the remaining water while the mixture ultimately breaks down into gaseous products, oils, and carbon.

The principal advance of these two-stage methods was to permit generation of higher quality and more useful mixtures of oils than any of the previous single stage processes. However, the need to evaporate a significant portion of the water still entails a substantial energy penalty, and the products of such methods still suffer from problems of contamination from materials such as sulfur- and chlorine-containing compounds. Additionally, there are increases in efficiency of production of hydrocarbon products that would be desirable to achieve. Hitherto, the complex chemistries that have been occurring within the reaction mixture have not been well understood and certain coproducts have been produced in unwanted amounts. Thus, these two stage methods have been difficult to make commercially viable.

Accordingly, there is a need for a method of processing waste and low-value products to produce useful materials in reliable purities and compositions, at acceptable capital and operational cost.

SUMMARY OF THE INVENTION

The present invention addresses the processing of waste and low-value products to produce useful materials in reliable purities and compositions, at acceptable cost, without producing malodorous emissions, and with high energy efficiency. In particular, the invention comprises a multi-stage process that converts various feedstocks that otherwise have little commercial value or use, to useful materials including gas, oil, specialty chemicals (such as fatty acids), fertilizer, and carbon solids. The invention further comprises an apparatus for performing a multi-stage process of converting waste products into useful materials, and at least one oil product that arises from the process. The apparatus and process of the present invention are particularly applicable to processing organic and inorganic waste, including offal from poultry (such as turkey, chicken, ostrich), cattle, pigs, fish, and other waste products such as animal manures, grease, vegetable oil, and municipal sewage sludge.

In overview, a process according to the present invention subjects a suitably prepared feedstock to heat and pressure, separates out various components of the resulting feed, then further applies heat and pressure, to one or more of those components. Various materials that are produced at different points in the process of the present invention may be recycled and used to play other roles within the process of the present invention.

The present invention includes a process for converting a feedstock into at least one useful material, comprising: preparing a slurry from the feedstock; reacting the slurry in a first reaction to produce a reacted feed comprising at least one reacted solid product, at least one reacted liquid product, and water; separating the at least one reacted solid product, the water, and the at least one reacted liquid product from the reacted feed; and converting the at least one reacted liquid product into at least one useful material in a second reaction. The conditions of the first reaction preferably include addition of one or more reagents that suppress hydrolysis of carbohydrates, and encourage dissociation of amines to liberate ammonia.

The present invention additionally includes an apparatus for converting a feedstock into at least one useful material, comprising: a pre-treatment unit configured to produce a heated slurry from the feedstock; a first stage reactor communicating with the vessel to receive the heated slurry, the first stage reactor configured to subject the heated slurry to a first increased temperature and a first increased pressure to produce a reacted feed that comprises at least one reacted solid product, at least one reacted liquid product, and water; at least one separation unit communicating with the first stage reactor to receive the at least one solid product, at least one liquid product, and water, the unit configured to separate out the at least one reacted solid product, the water, and the at least one reacted liquid product; and a third stage reactor communicating with the separation unit to receive the at least one reacted liquid product, the third stage reactor configured to subject the at least one reacted liquid product to a second increased pressure and a second increased temperature, thereby converting the at least one reacted liquid product to at least one useful material. In a preferred embodiment, the pre-treatment unit comprises a preparation unit, including a slurrying device to create a feedstock slurry from the feedstock; a vessel communicating with the feedstock preparation unit to receive the feedstock slurry from the feedstock preparation unit, and additional equipment such as a pump and a heat exchanger configured to pressurize and heat the slurry to produce a heated slurry. In another preferred embodiment, the first stage reactor is configured to accept one or more reagents that suppress hydrolysis of carbohydrates, and encourage dissociation of amines to liberate ammonia.

The present invention additionally includes a process for converting a feedstock into at least one useful material, comprising: preparing a slurry from the feedstock; passing the slurry through a heat exchanger, wherein one or more gases is vented, to produce a conditioned slurry; reacting the conditioned slurry in a first reaction, wherein steam and gas is liberated, to produce a reacted feed comprising at least one reacted solid product, at least one reacted liquid product, and water, wherein the reacted solid product comprises at least one mineral; lowering a temperature, and lowering a pressure, of the reacted feed, to produce an intermediate feed; separating the at least one mineral from the intermediate feed, thereby producing a mixture comprising at least one reacted liquid product, and water; diverting said water to storage; subjecting said at least one reacted liquid product to a second reaction wherein carbon solids and a mixture of hydrocarbon vapor and gases are produced. The conditions of the first reaction preferably include addition of one or more reagents that suppress hydrolysis of carbohydrates, and encourage dissociation of amines to liberate ammonia.

The present invention additionally includes a process for converting municipal sewage sludge into at least one useful material, comprising: preparing a slurry from the municipal sewage sludge; reacting the slurry in a first reaction to produce a reacted feed comprising at least one reacted solid product, and at least one reacted liquid product, and water, wherein the first reaction additionally includes use of one or more reagents that suppress hydrolysis of carbohydrates, and encourage dissociation of amines to liberate ammonia; separating said at least one reacted solid product, said water, and said at least one reacted liquid product from said reacted feed; converting said at least one reacted liquid product into at least one useful material; and in a second reaction, converting said at least one solid product into a mixture of hydrocarbon oils, fuel gas and a mixture of minerals and carbon.

The present invention also includes a process for converting turkey offal into at least one useful material, comprising: preparing a slurry from the turkey offal; reacting the slurry in a first reaction to produce a reacted feed comprising at least one reacted solid product, and at least one reacted liquid product, and water, wherein the first reaction additionally includes use of one or more reagents that suppress hydrolysis of carbohydrates, and encourage dissociation of amines to liberate ammonia; separating the at least one reacted solid product, the water, and the at least one reacted liquid product from the reacted feed; and in a second reaction, converting the at least one reacted liquid product into a mixture of hydrocarbon oils, fuel gas, and carbon.

The present invention further comprises a fuel oil manufactured by a process, wherein the process comprises: preparing a slurry from a carbon-containing feedstock; reacting the slurry in a first reaction to produce a reacted feed comprising at least one reacted solid product, at least one reacted liquid product, and water, wherein the first reaction additionally includes use of one or more reagents that suppress hydrolysis of carbohydrates, and encourage dissociation of amines to liberate ammonia; separating said at least one reacted solid product, said water, and said at least one reacted liquid product from said reacted feed; converting said at least one reacted liquid product into the fuel oil in a second reaction.

BRIEF DESCRIPTION OF THE DRAWINGS

FIGS. 8A and 8B show use, respectively, of a third stage reactor and a cooler/condenser with a process according to the present invention.

DETAILED DESCRIPTION

Figure 1:
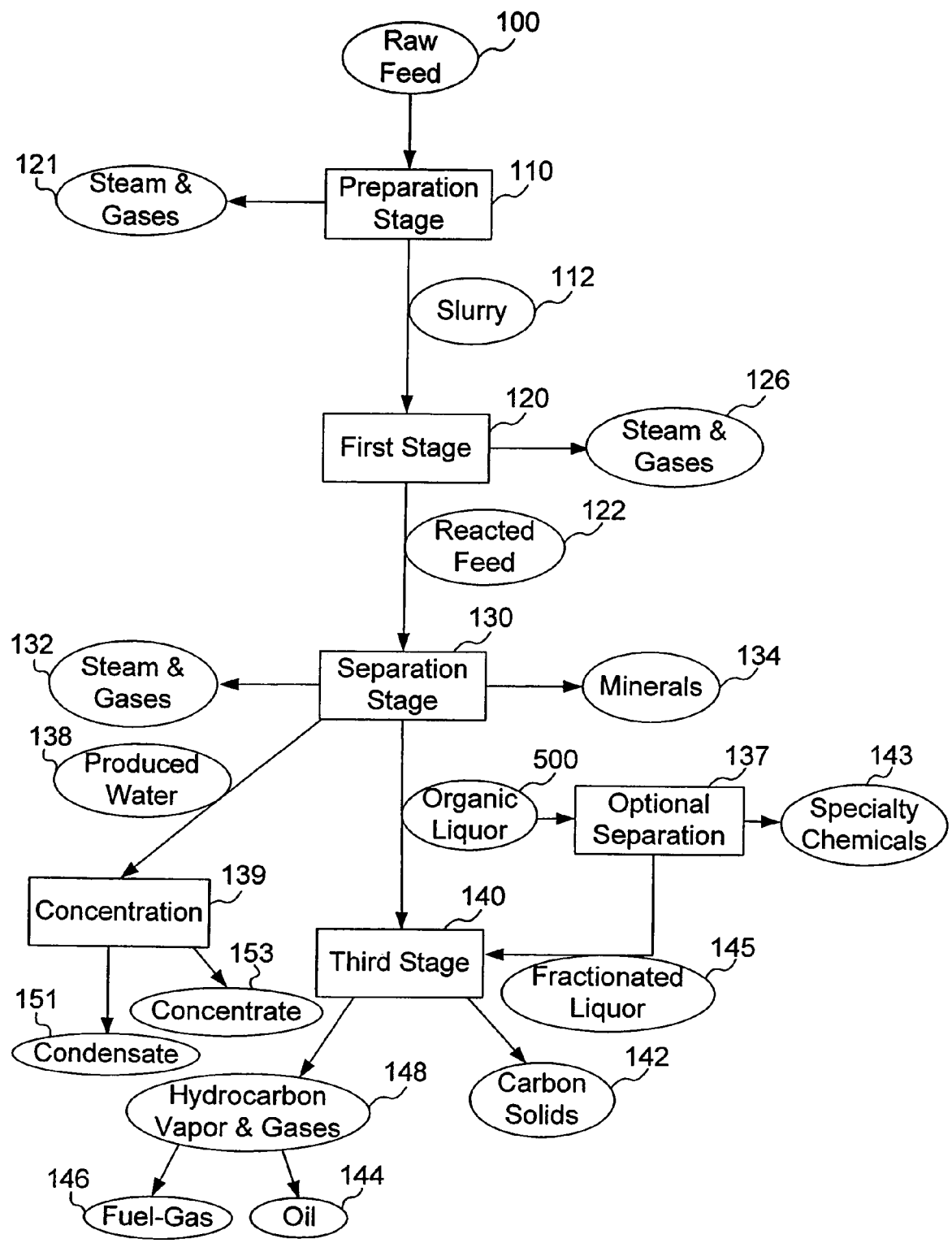
FIG. 1 shows a flow-chart of an overall process according to the present invention.

The process of the present invention is directed to producing one or more useful materials from low-value or waste products generated by society at large, either from ordinary domestic practices, or from commercial operations. Typically the process of the present invention is applied to waste products, or other low-value products, for example grease, that contain a substantial proportion of organic materials. However, the present invention may be applied to convert other products, not normally considered low-value, to higher-value products.

Organic materials as used herein are those commonly understood by one of ordinary skill in the art. In particular, for use with the present invention, organic materials are those materials whose constituent elements include carbon in combination with one or more other elements such as hydrogen, oxygen, nitrogen, sulfur, and phosphorous, and the halogen elements, in particular fluorine, chlorine, bromine, and iodine. For the purposes of the present invention, organic materials also include compounds that contain carbon in combination with elements such as arsenic, selenium, and silicon, as well as salts of organic molecules, and complexes of organic molecules with metals such as, but not limited to, magnesium, mercury, iron, zinc, chromium, copper, lead, aluminum, and tin. Many organic materials used with the present invention come from biological sources and comprise proteins, lipids, starches, nucleic acids, carbohydrates, cellulose, lignin, and chitin, as well as whole cells. Other organic materials for use with the present invention, have man-made, or synthetic origin, such as plastics, and other petroleum-derived products.

In the process of the present invention, heat and pressure are applied to a feedstock at the levels needed to break the long molecular chains of the feedstock's organic components. Thus, feedstock material is broken down at the molecular level to one or more constituent materials. In the process, the feedstock is transformed from a cost or low value to a profit, or significant cost reduction, or higher value. Importantly, the process is able to destroy pathogens.

The basic process of the present invention is designed to handle potentially any waste or low-value product, including: by-products of food manufacture and distribution such as turkey offal, fryer oils, corn stalks, rice hulls, waste scraps, last-press edible oils such as canola, soybean, palm, coconut, rape seed, cotton seed, corn, or olive oil, and other oils, food processing wastes, and seafood industry wastes; by-products of paper and other wood industry manufacturing, such as cellulose and lignin by-products, and paper-pulp effluent; yard waste such as leaves and grass clippings; harbor-dredged sediments; post-consumer plastics and electronics, such as old computers; municipal solid waste; oil-refinery residues; industrial sludges; bagasse; seaweed; milling waste; black liquor; coal refinery wastes; tar sands; shale oil; drilling mud; cotton waste; agricultural processing wastes such as animal manures; infectious medical waste; biological pathogens; and even materials such as anthrax spores that could be used to make biological weapons. It is to be understood that the foregoing list of materials is not an exhaustive list. In the foregoing list, bagasse is a byproduct from processing of sugar cane, and black liquor is a byproduct of chemical wood-pulping that results from dissolving wood chips, liberating the lignin, and freeing the fibers to give rise to a lignin and hemi cellulose solution.

Waste products for use with the present invention are typically byproducts or end-products of other industrial processes, commercial preparations, and domestic or municipal uses, that typically have no other immediate use and/or which are ordinarily disposed of. Low-value products may similarly be byproducts or end-products of other industrial processes, commercial preparations, and domestic or municipal uses, but are typically materials that have very low re-sale value and/or which require some further processing to be converted into something of use.

When used with the process of the present invention, waste and low-value products are typically referred to as feedstocks or as raw feed. It is also to be understood that the raw feed used with the process of the present invention can comprise waste and/or low-value products from a number of sources, and of a number of different types. For example, food-processing wastes could be combined with agricultural processing wastes, if convenient, and processed simultaneously.

Still other exemplary raw feed materials for use with the present invention include municipal sewage sludge and mixed plastics as might be obtained from a municipal recycling depot.

Waste and low-value materials processed by embodiments of the present invention are generally converted into three types of useful materials, all of which are both valuable and are not intrinsically harmful to the environment: high-quality oil; clean-burning gases; and purified solids including minerals, and carbon solids that can be used as fuels, fertilizers or raw materials for manufacturing. Additionally, various side-streams are produced during the process of the present invention, including in some instances to concentrates similar to "fish solubles." Typically, useful materials are considered to be those that have a higher economic value than the waste, low-value or other materials that served as the feedstock. Such useful materials may have, for example, higher calorific content, or may have a wider range of applications than the feedstock from which they were derived.

Figure 2A:
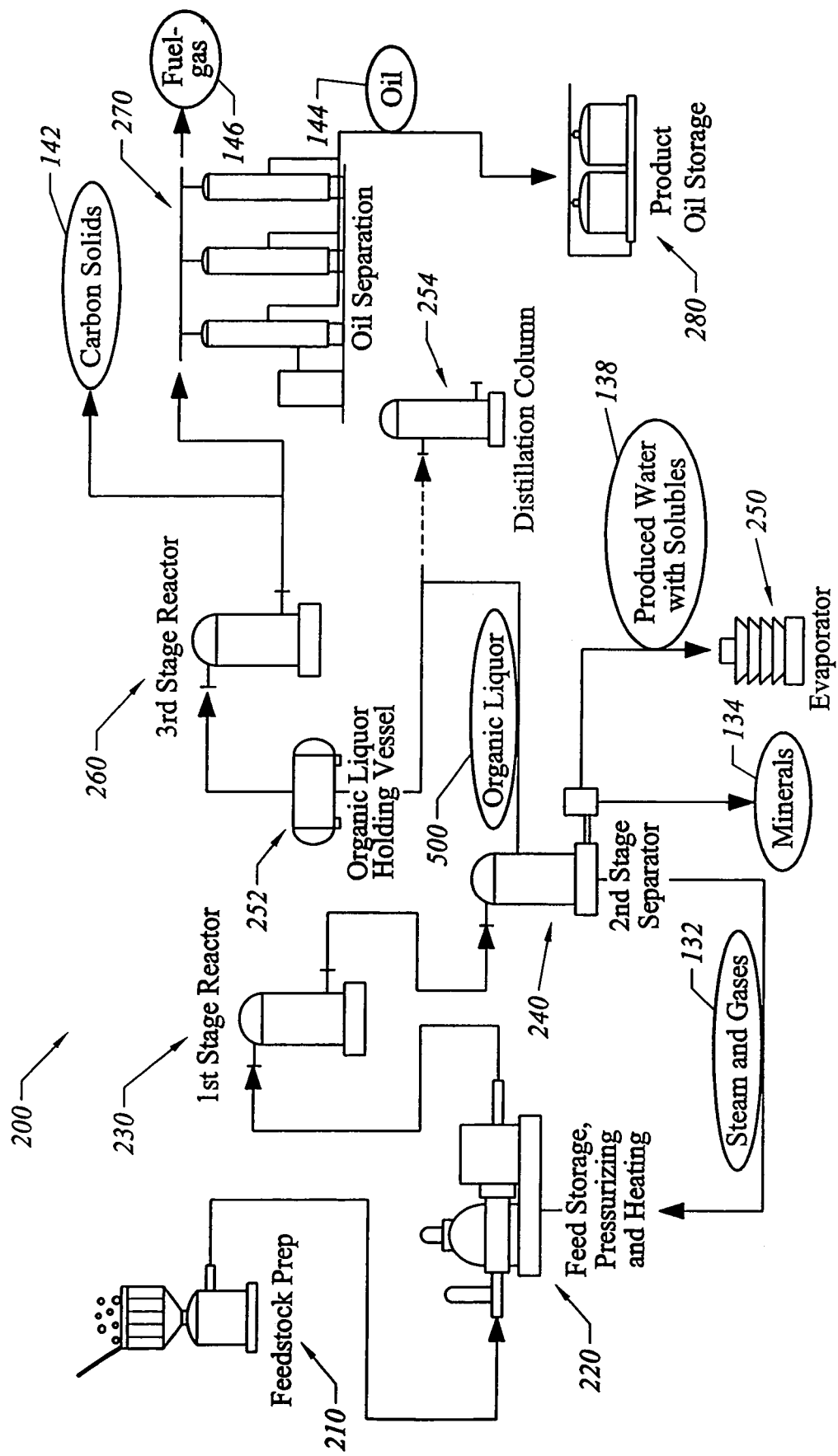
FIG. 2A shows an apparatus for performing a process of the present invention.

The process of the present invention comprises a number of stages, as illustrated in FIGS. 1 and 2. FIG. 1 shows, in outline, principal features of an embodiment of the process of the present invention. FIG. 2A shows an exemplary apparatus 200 for carrying out a process according to the present invention.

The raw feed 100, shown in FIG. 1, may potentially be any waste product or low-value organic and/or inorganic stream. Preferably, the raw feed contains a substantial amount of carbon-containing material.

Raw feed 100 is subjected to a preparation stage 110. An aspect of the preparation stage is to reduce the size of the raw feed using pulping and other grinding technologies to a size suitable for pumping. The preparation stage may comprise one or more steps, and may comprise adding materials to, or driving materials off from the raw feed, and results in a slurry 112 that is passed to a first stage 120. Slurrying may involve adding water (or other suitable fluid) to raw feed 100, depending upon its initial water content. Use of a slurry is beneficial because wet grinding, as in the preparation stage 110, reduces friction and energy consumption, and because a slurry may be easily transferred by pumps from one vessel to another. Suitable slurrying devices include: a pulper, an in-line grinder, or a maserator. A mixture of steam and gases 121 is given off from preparation stage 10. Other aspects of the preparation stage that may be beneficially applied to feedstocks containing animal body parts are described in copending application Ser. No. 10/954,691, filed Sep. 29, 2004, entitled "Apparatus And Process For Separation of Organic Materials From Attached Insoluble Solids, and Conversion Into Useful Products", by Adams, et al., the disclosure of which is incorporated herein by reference in its entirety.

In a first stage 120, the slurry is subjected to heat and increased pressure wherein the slurry undergoes a first reaction, also called a first stage reaction. Such conditions of heat and pressure lead to breakdown of the cell structure of biological components of the slurry, to release constituent molecules such as proteins, fats, nucleic acids, and carbohydrates. Additionally, many polymeric organic materials are hydrolyzed by water in the slurry to mixtures of simpler organic products. In particular, fats may be partially split to give floatable organic materials such as fatty acids (containing carboxylic acid groups), and water soluble glycerols (i.e., molecules containing 3 hydroxyl groups). Proteins are typically broken down into simpler polypeptides, peptides, and constituent amino acids. Carbohydrates are largely broken down into simpler, water soluble, sugars. Furthermore, the presence of water in the first stage is advantageous because it helps convey heat to the feedstock.

It is to be understood that the terms react, reacting and reaction, when used in conjunction with embodiments of the present invention, can encompass many different types of chemical changes. In particular, the term reaction can encompass a chemical change arising from the combination or association of two or more species that give rise to one or more products, and can encompass other types of decompositions or conversions that involve the breakdown or transformation of a single species, as induced by conditions of temperature, pressure, or impact of electromagnetic radiation, and can further encompass transformations involving a solvent, such as a hydrolysis. It is further to be understood that when the term "reaction", or "react" is used herein to describe a process, or a stage in a process, then more than one chemical change can be occurring simultaneously. Thus, a reaction can simultaneously involve a hydrolysis and a decomposition, for example.

The chemical environment during the first reaction is complex and encompasses both dissociation of materials and simultaneous reformation of other materials from the resulting components. As is further discussed herein, under the conditions employed in the first reaction fats (principally triglycerides) will typically hydrolyze. Proteins will denature into their constituent amino acids and small peptides, all of which are amines. The presence of amines in the mixture is problematic because amines facilitate formation of an emulsion and help to stabilize it. Thus, small particles of insoluble—usually inorganic—material are held in suspension, a fact which hinders separation of the various components of the mixture. Ideally, then, amines should be broken down as soon as possible. Carbohydrates will also tend to hydrolyze to form sugars but the sugars then also undergo a reaction known as the Maillard reaction in which they react with the amines to form glycosylamines and other products, many of which are insoluble and polymeric. The end result is the presence of compounds that further enhance the propensity to form an emulsion.

Furthermore, many of the organic materials that are to be converted to useful products such as oil by the process of the present invention have high oxygen content—e.g., carbohydrates. Such materials tend to give off a lot of $CO_2$ and eventually carbon, both of which are undesirable. Instead, it would be preferred if as much carbon as possible went into a hydrocarbon product. To this end, it is preferable to introduce an oxygen scavenger into the system that takes out the oxygen from the raw feed, and ensures that it is diverted into a more useful byproduct (i.e., other than $CO_2$), thereby permitting more of the carbon content to be converted into hydrocarbons.

Accordingly, it is consistent with the present invention that one or more reagents is added to the first stage reaction in order to liberate ammonia—and thereby discourage emulsion—formation, as well as to suppress decarboxylation reactions. In a preferred embodiment, elemental sulfur, and elemental sulfur are introduced into the first stage reaction.

A mixture of steam and gaseous products 126 is typically liberated from the slurry in the first stage 120. The reacted feed 122 resulting from the first stage typically consists of a mixture of reacted solid products and a mixture of reacted liquid products. These various products are typically characterized as an oil phase, a water phase, and a wet mineral phase. The water phase and the oil phase typically contain various dissolved organic materials. The mixture of steam and gases 126 produced in the first stage 120 is preferably separated by a condenser, and the steam is used to pre-heat incoming slurry.

The reacted feed 122 is then subjected to a separation stage 130 in which a further mixture of steam and gases 132 is driven off, and a mixture of minerals 134 or other solid materials is separated out. Preferably, the solid materials obtained at this stage do not comprise carbon solids, unless carbon solid was present in the input feedstock. Separation stage 130 may comprise more than one individual separation.

The residual material from separation stage 130 consists of a mixture of liquid products that includes produced water 138 (water with solubles) and an organic liquor 500. The organic liquor 500 is typically a liquid that contains a mixture of carbon-containing species such as reacted liquid products from the first reaction. Preferably, most of the produced water 138 is separated off, and a liquid product such as the organic liquor 500 is directed to a third stage 140. Thus, the organic liquor preferably comprises a reacted liquid product, separated from water and in most instances also separated from reacted solid product. The produced water 138 contains numerous compounds including sulfur- and chlorine-containing materials and is preferably diverted for concentration 139. It is desirable to separate out such compounds and, in preferred embodiments, concentration gives rise to a condensate 151 (whose purity is usually better than that of municipal-strength wastewater), and a concentrate 153 (that, in many instances, can be used as liquid fertilizer similar to fish solubles).

Some of organic liquor 500 may be diverted to an optional separation 137 to form specialty organic chemicals 143 such as fatty acids or amino acids, for example via fractional distillation of the organic liquor. Residual fractions, fractionated liquor 145, often called 'heavy liquor', that comprises fractions that are not useful as specialty chemicals, may be redirected to third stage 140.

When the feedstock is municipal sewage sludge, the reacted feed 122 from the first stage reaction typically comprises produced water, a solid matrix of organic and inorganic material, and a small amount of organic liquor. The produced water from municipal sewage sludge is then diverted for concentration to form a product that finds application as a fertilizer.

In a third stage 140, the organic liquor 500 is subjected to conditions wherein it undergoes a second reaction. It is also possible that the organic liquor contains some quantity of reacted solid product that is also passed to the third stage. Together, the organic liquor and reacted solid product may be referred to as a solid matrix. In the second reaction, the organic liquor is converted to a mixture of useful materials that usually includes carbon solids 142, and a mixture of hydrocarbons that is typically released as hydrocarbon vapor and gases 148. Such a conversion may involve a decomposition of one or more materials in the organic liquor. Suitable conditions in the third stage typically use temperatures that are elevated with respect to the first stage, and use pressures that are reduced with respect to the first stage. The third stage typically does not involve the use of added water.

Carbon solids 142 are typically similar to coke, i.e., usually hard carbonaceous materials with a high calorific value suitable for use as a fuel. Carbon solids 142 preferably contain little, if any, non-combustible minerals that typically result from the incineration of carbon-containing materials in an oxygen-deficient atmosphere. The mineral content of carbon solids 142 is preferably less than 10% by weight, more preferably less than 5% by weight, still more preferably less than 2% by weight, and most preferably less than 1% by weight. Where carbon solids 142 contain minerals, they may also be described as a carbon-mineral matrix.

The hydrocarbon vapor and gases 148 are referred to as "bio-derived hydrocarbons" whenever biological material is the feedstock to the process of the present invention. The hydrocarbon vapor and gases can be variously referred to as "tire-derived", "rubber-derived" or "plastic-derived" if the raw feed stock comprises tires, rubber, or plastics, respectively. Hydrocarbon vapor and gases 148 typically comprise hydrocarbon gases, with possibly some trace impurities of non-hydrocarbon gases. The hydrocarbon gases include gases such as fuel-gas 146; the hydrocarbon vapors may be readily condensed to liquids or oils 144 such as the lighter constituents of #2 diesel oil. One of ordinary skill in the art understands that a #2 diesel oil is an oil with a relatively low viscosity or density.

When the feedstock is municipal sewage sludge, the solid products from the third stage typically comprise a mixture of hydrocarbon oils, fuel gas, and a mixture of minerals with carbon, in solid form.

It is to be understood that the operating parameters of the process of the present invention may be adjusted in one or more instances in order to accommodate different types of raw feed materials. For example, in the context of raw feed such as turkey offal, the major components are animal fats, proteins, carbohydrates, and minerals. Thus, the balance of the major components may determine some aspects of the operating conditions of the present invention. Furthermore, the temperature ranges of the first and third stage reactors can be controlled to produce specific products, thereby maximizing the economic value that can be obtained from the yield of various products.

An apparatus 200 for carrying out a process according to the present invention is shown in FIG. 2A. Based on the teachings of the present invention, the assembly of the various components of apparatus 200 would be within the capability of one of ordinary skill in the art of process engineering or chemical engineering. Accordingly, such technical details as would be familiar to an artisan of ordinary skill are omitted from the present description.

Feedstock preparation and slurrying may be carried out in a feedstock preparation apparatus 210. After feed preparation and feed slurrying, the slurry is passed to a low pressure vented vessel 220 referred to as a feed storage tank. Preferably the feed is subjected to heating in or before the feed storage tank to produce a heated slurry that is optionally subjected to pressurizing prior to entering the first stage reactor. Such heating and pressurizing typically take place in equipment that comprises a vessel to retain the slurry, a pump for increasing the pressure of the slurry, and a heat exchanger to heat the slurry. Typically conditions of about 140° F. and 1 PSI are employed, to keep the feed slurry in a liquid state, and to limit biological activity. In a preferred embodiment, the feed storage tank comprises a first tank and a second tank. In such a preferred embodiment, the first tank is heated to a temperature of about 140° F. (about 60° C.) and subjected to a pressure of about 1 p.s.i. Such conditions in the first tank effectively bring about a cessation of biological activity. In an exemplary embodiment, such a first tank may have a capacity of about 1,000,000 U.S. gallons; thus, for a throughput of 100-150 gallons/minute, the effective residence time in such a tank is about 700 minutes. The second tank in such an embodiment may be maintained at a temperature of about 280° F. and subjects the contents to a pressure of up to about 100 p.s.i. The pressure is generally slightly above the saturation pressure of the mixture at a given temperature. For example, the saturation pressure of the mixture is 66 p.s.i. at about 300° F. (about 150° C.). The conditions in the second tank are typically harsh enough to breakdown proteinaceous materials in the slurry, to loosen the slurry, and to drive off ammonia. The capacity of the second tank is typically less than that of the first tank, and may be as small as 2,500 U.S. gallons. Thus, in one embodiment, a flow rate of about 40 gallons per minute gives a residence time of about an hour in the second tank. Longer, preferred residence times for particular feedstocks, for example of several hours in the second tank, may be achieved with lower flow rates.

Figure 2B:
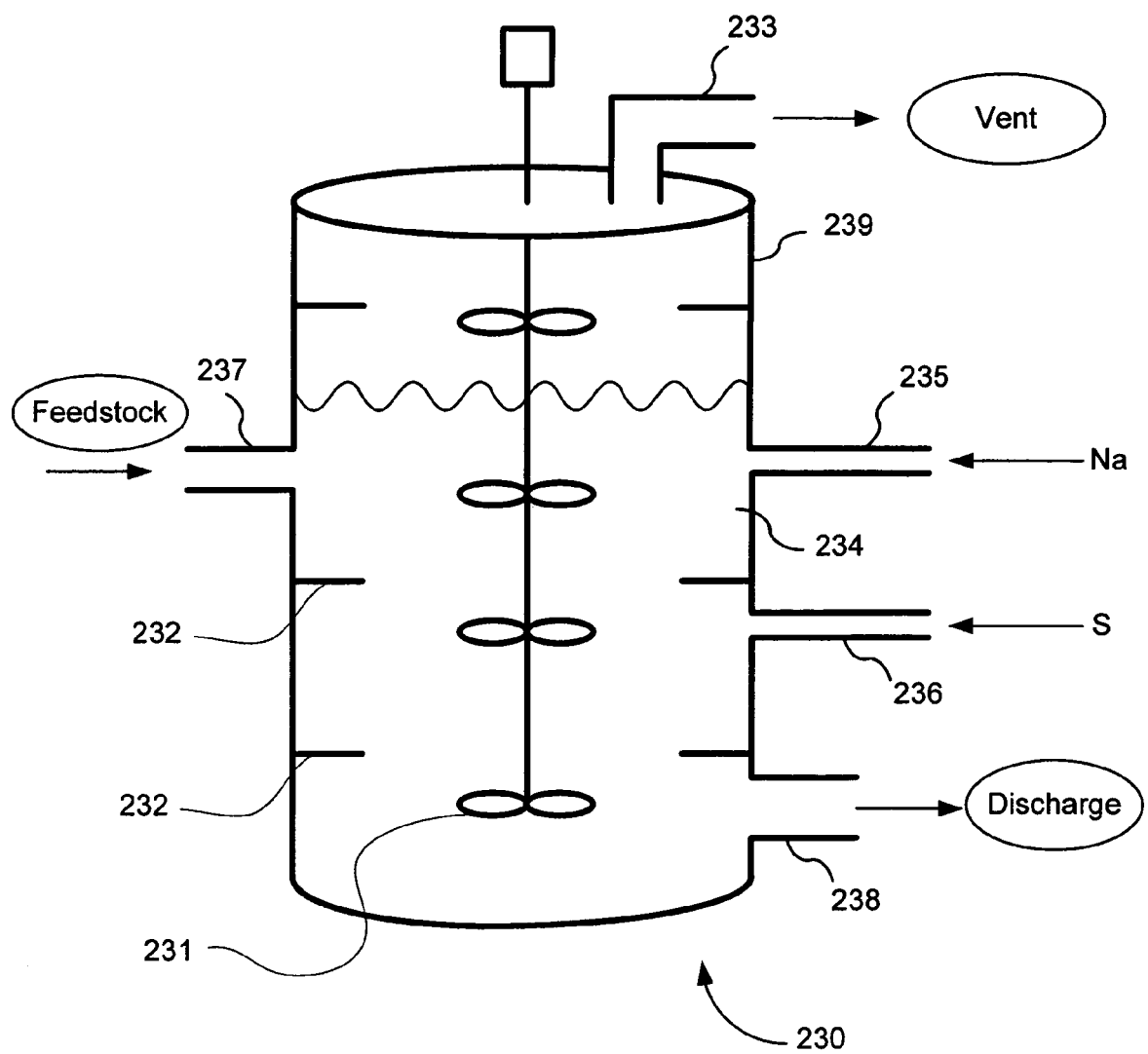
FIG. 2B shows an embodiment of apparatus for performing a first reaction, wherein the apparatus is configured to accept one or more reagents that suppress hydrolysis of carbohydrates, and encourage dissociation of amines.

The first stage of the present invention is carried out in a first stage reactor 230, a preferred embodiment of which is shown in FIG. 2B. According to the embodiment shown in FIG. 2B, first stage reactor 230 comprises a vessel 239, which is preferably a multi-chamber vessel so that there is a narrow distribution of residence times of the constituent materials of the slurry 234. Preferably the vessel is equipped with baffles 232, and a multi-blade motorized stirrer 231 that can simultaneously stir the slurry in each of the chambers. In a preferred embodiment, there are four chambers in such a vessel. In another preferred embodiment, the heating of the slurry takes place in several stages ahead of this vessel. First stage reactor 230 is also preferably equipped with a vent 233, an input pipe 237 through which the slurry is input, and a discharge pipe 238 through which reacted feed can be piped out of the vessel. First stage reactor 230 also additionally has a first pipe 235 through which a reagent such as molten sodium may be input to the reaction mixture, and a second pipe 236 through which another reagent, such as molten sulfur, may be input. Although FIG. 2B shows input and discharge pipes disposed at different heights along, and on different sides of, vessel 239, one of ordinary skill in the art will appreciate that FIG. 2B is purely a schematic and that other configurations of the input and discharge pipes are consistent with the practice of the present invention. In an alternate embodiment, the first stage reactor can also be an augured reactor.

For the purpose of suppressing the quantity of amines present in the reaction mixture, additional reagents are preferably introduced to the first stage reaction. As is further discussed herein, such reagents preferably include elemental sulfur, and elemental sodium. Because they have low melting temperatures (~120° C. and 98° C. respectively) these materials may be metered and controllably added to the reaction mixture. It is preferable, then that the vessel for the first stage reaction is a vertically oriented vessel to facilitate controlled degassing of gases such as ammonia, carbon monoxide, or carbon dioxide, sulfur-containing gases such as $H_2S$, or chlorine containing compounds.

The flashing of the reacted feed after the first reaction can be achieved in a flash vessel 240 (a "second stage separator") with a vent. Preferably the pressure in the flash vessel 240 is considerably lower than that in the first stage reactor 230. In one embodiment, the pressure in the flash vessel is about 300 psi, where the pressure in the first stage reactor is around 600 psi.

Various equipment can be used to achieve various second stage separations of the feed that comes out of the first stage reactor 230. Preferably such separations provide a mixture of steam and gases 132, organic liquor 500, minerals 134, and produced water with solubles 138. Steam and gases 132 are preferably diverted back to the preparation stage to assist with feed heating.

Separation of the minerals from the organic liquor and water can be achieved with centrifuges, hydrocyclones or with a static tank. Drying of the minerals 134 can be achieved with, for example, a drying kiln or other mineral drier such as a "ring" dryer (not shown in FIG. 2A). (In an alternate embodiment, separation can be facilitated by adding a chemical to break the emulsion.)

Produced water with solubles 138, resulting from the separation of the organic liquor from the water, can be concentrated in an evaporator 250 of a type that is typically available in the industry. The organic liquor 500 that has been separated from the minerals and the water may be contained in an organic liquor holding vessel 252 prior to transfer to the third stage reactor 260. Such a holding vessel may be an ordinary storage vessel as is typically used in the industry.

Some portion of the organic liquor 500 may be diverted to give one or more specialty chemicals. Typically this involves subjecting the organic liquor to fractional distillation. The organic liquor that is subjected to fractional distillation is typically distilled in a distillation column 254. The organic liquor may be subjected to an acid wash to separate out trace amino acids before passing it to the distillation column. More volatile materials from the organic liquor, such as fatty acids, are distilled off and collected. Any heavier materials such as non-volatilized fats and fat derivatives that are found in the bottom of the distillation column are passed on to the third stage reactor 260.

The organic liquor that comes from the second stage separation is also passed to the third stage reactor 260 wherein a second reaction takes place in which the organic liquor is converted into one or more useful materials such as oil, and carbon solids 142. The oil that comes out of the third stage reactor may be subjected to further separation in a separator 270, to produce oil 144 and fuel-gas 146. The separation may comprise condensing the oil in various steps, and diverting it to oil storage 280 in a storage vessel. The carbon solids 142 that come from the third stage reactor are cooled and may also be stored, or further heated and then treated to activate them according to methods that are known to one of ordinary skill in the art. For example, the carbon solids may be heated in an additional reactor, and be activated by the injection of superheated steam.

As discussed hereinabove, exemplary raw feed materials include waste products from the agricultural and food processing industries. Such waste products can comprise animal parts such as wings, bones, feathers, organs, skin, heads, blood and necks, soft tissue, claws and hair. Typical animal parts are those found in turkey offal and remnants of carcasses from slaughterhouses. In general it is intended that body parts from any kind of animal can be used with the present invention. For example, such animals include but are not limited to: turkey, other poultry including chickens, ducks, geese, swine, horse, cattle, sheep, fish, whale, llama, alligator, kangaroo, and elk. Other waste products from the food processing industry that are suitable for processing with the methods of the present invention include unused grease from fast food establishments such as burger franchises, and materials such as dissolved air flotation ("DAF") sludge from food processing plants. Agricultural waste products can include animal dung or manure from sheep, pigs, and cows, and also other materials such as chicken litter and crop residuals. In an exemplary embodiment illustrated in FIGS. 3-5, raw feed 100 is a food processing byproduct such as turkey offal.

Figure 3:
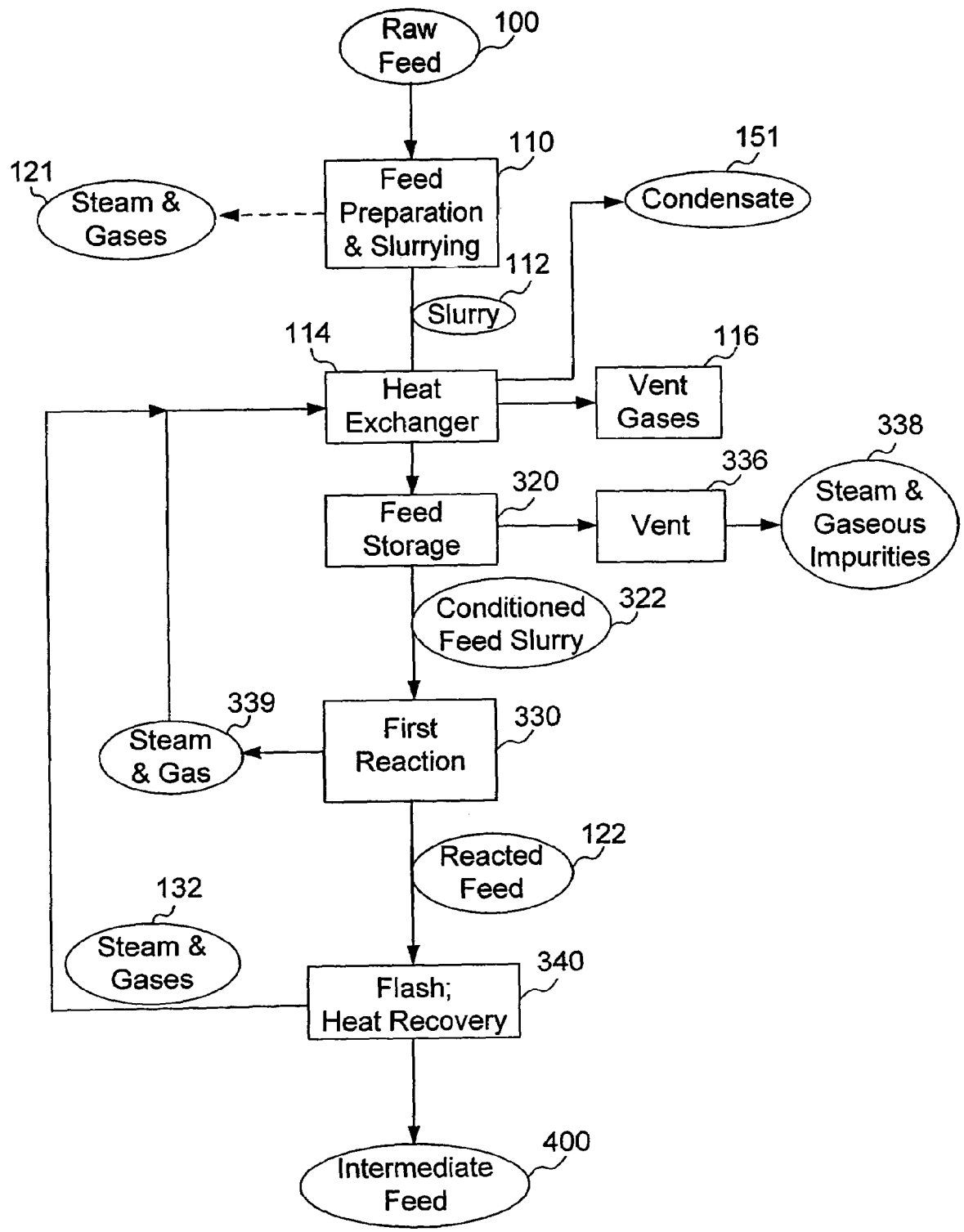
FIG. 3 shows a flow-chart of a preparation and first stage reaction of a process of the present invention.

As shown in FIG. 3, raw feed 100 is initially subjected to preparation and slurrying 110 to produce a feed slurry 112, accompanied by steam and gases 121. Slurry 112 may be transferred to feed storage 320 in a feed storage tank ("FST" or homogenizer) via a heat exchanger 114. In the FST, the contents are preheated, typically to a temperature between about 60° C. and about 150° C., in order to lower viscosity, biologically inactivate the slurry, and help mixing. The contents are mixed in the FST to produce conditioned feed slurry 322, a relatively homogeneous feed suitable for passing to the first stage reactor. During feed storage, steam and gaseous impurities 338 are preferably vented 336. Thus, one advantage of the present invention is that degassing occurs in the FST so that unwanted gaseous impurities are removed at an early stage in the overall process of the present invention. Feed slurry 112 may remain in feed storage 320 for any convenient time until it is due to be further processed by the methods of the present invention. Preferably, the FST supplies a constant feed stream to a high-pressure slurry pump that pressurizes the feed and transports it to the first stage reactor.

For raw feed materials that contain significant amounts of ammonia ($NH_3$), such as turkey offal, it is advantageous to remove the free ammonia, either during preparation 110, in which case it is one component of steam and gases 121, or during storage 320, where it is vented along with steam and gaseous impurities 338. One source of ammonia is the breakdown of uric acid found in residual quantities of urine that are often present in aggregates of animal body parts. Methods of removing ammonia are within the knowledge of one of ordinary skill in the art and include, but are not limited to, separation of the urine content prior to slurrying, use of enzymatic degradation, and application of heat. Additionally, ammonia can be converted by acidification to a salt such as ammonium sulfate, or ammonium phosphate. In a preferred embodiment, the FST comprises two vessels maintained at different conditions. The first such vessel performs the role of storage; the second vessel effects the breakdown of proteins, and releases ammonia.

The conditioned feed slurry 322 that emerges from feed storage 320 is subjected to a first reaction 330, wherein water content in the conditioned feed slurry 322 effects a hydrolysis of many of the biopolymers present. Sufficient agitation (provided by mixers and/or recirculation devices) is provided so that solids are kept in suspension. The first reaction typically takes from about 5 to about 60 minutes. The output from the first reaction is a reacted feed 122. Typically steam and gas 339 are also released from the first reaction.

In the first reaction 330, some degasification takes place in which partial removal of nitrogen and sulfur compounds occurs, and deamination and decarboxylation reactions can take place in which significant quantities of protein also dissociate into products such as ammonia, and potentially carbon dioxide. In practice, for the process of the present invention, decarboxylation reactions are unwanted because the products, other than carbon dioxide, are amines which tend to be water soluble, and volatile. Additionally, any loss of carbon to $CO_2$ at this stage potentially deprives the hydrocarbons resulting at the end of the process from a quota of carbon. Thus, in general, deamination reactions are preferred to decarboxylation reactions, and the reacted liquid products obtained from the first stage typically include carboxylic acids when the feedstock includes material such as proteins and fats. Accordingly, since decarboxylation reactions typically occur at higher temperatures than deaminations, the first reaction is preferably run at the lowest temperature possible at which fat molecules are split. As an alternative, the pH in the first stage can be shifted by adding acid, thereby discouraging decarboxylation reactions.

Since the amines formed from protein decomposition in the first stage reaction support an emulsion, and since the hydrolysis products from the carbohydrates undergo Maillard reactions to give insoluble residues, it is preferable to also add reagents that break down the amines. Preferred reagents include elemental sulfur, and elemental sodium, as further discussed herein.

An effective way to drive off the amino groups from the amines, as ammonia ($NH_3$), would be to add an acid. Although sulfuric acid, $H_2SO_4$, would ordinarily be an effective acid for this purpose, it is also a dehydrating agent and, under the conditions of the first stage reactor, it will also react with the sugars to produce an undesirable blackened charred mass. Accordingly, some way of removing the amino groups other than direct addition of $H_2SO_4$ is preferred.

Elemental sulfur may be handled relatively easily however and, since its melting temperature is around 120° C., it may be injected quite practically into the stream of reagents. Elemental sulfur consists of cyclic molecules having the structural formula $S_8$. When heated to the temperatures employed in the first stage reaction, the $S_8$ molecules break open and react with oxygen containing molecules in the reaction mixture to form $SO_2$ and $SO_3$. Once sulfur has reacted to form sulfur dioxide and sulfur trioxide a further reagent is required to promote a reaction to create $H_2SO_3$ and $H_2SO_4$ in situ.

One way to achieve further more desirable reactions in situ is to introduce sodium metal. Sodium acts as a powerful reducing agent and has two principal effects: it will react exothermically with any water present to produce hydrogen gas ($H_2$) and sodium hydroxide. It will also, however, scavenge an additional oxygen from various components of the reaction mixture—such as carbohydrates—which will combine with any $H_2SO_3$ and residual sulfurous oxides to give $H_2SO_4$ which will largely stay in the aqueous phase of the mixture. The acid will cause the proteins and amino acids to deaminate, and the hydrogen liberated by the sodium metal will combine with the free amine groups to give ammonia gas. Other byproducts from these reactions include sulfates—such as ammonium sulfate, $(NH_4)_2SO_4$—which are desirable because they can be used in fertilizers.

Sodium is economic to work with and, despite its known reactivity, can also be used safely, as evidenced by its deployment in other large scale industrial processes. In particular, it may also be stored under oil and piped into the reactor at easily attainable temperatures just above its melting point. It is also relatively easy to obtain and may be produced by electrolysis of a sodium salt, of which sodium chloride is the most abundant.

Ultimately, the presence of the two reagents, sulfur and sodium, creates a reducing environment. Such an environment is desirable because preferred end products of the process the present invention are hydrocarbons. Such products have to be created by removing oxygen that is bound to the carbon containing molecules in the original feedstock preferably without also losing carbon through $CO_2$ emissions.

Removal of the nitrogen and sulfur compounds at this stage, and the prior preheating stage, prevents formation of unwanted additional organic nitrogen compounds, more ammonia, and various sulfur compounds that might become undesirable components of the resulting bioderived hydrocarbons if allowed to become processed through the third stage reactor.

Typical conditions for carrying out the first reaction in this example are between 150° C. to 330° C., though preferably around 250° C., and around 50 atmospheres pressure, or about 600 psi, as may be obtained in a first stage reactor. Generally, the pressure in the first stage reactor is in the range 20-120 atmospheres. The total preheat and first stage heating time is up to around 120 minutes. Such conditions may be varied according to the feeds to be used. In one aspect of the present invention, as applied to feedstocks that contain large quantities of chlorine-containing materials, the operating temperature in the first stage is high enough, and is followed by washing steps, so that chlorine-containing products are removed.

Generally, the first reaction is carried out at temperatures in the range from about 150° C. to about 330° C. so that at least one of the following three transformations can be carried out. First, proteins are transformed to the individual amino acid residues of which they are composed. This can be achieved by hydrolyzing the peptide amide linkage between each pair of amino acid residues in the backbone of the protein at temperatures in the range about 150-220° C. Second, fat molecules can be broken down to fatty acid molecules, a process that can occur in the range of 200-290° C. Specifically, fats are hydrolyzed to split apart triglycerides to form free fatty acids and glycerol. Third, deamination and decarboxylation of amino acids can occur in the first stage. The carboxylic acid groups, if allowed to proceed to the third stage reactor, still attached to their respective amino acid moieties, can ultimately be converted to hydrocarbons at relatively mild operating conditions. Additionally, there may be some amino acids that are deaminated, a process that typically occurs in the temperature range 210-320° C. Thus, in the first stage alone, virtually all the protein present in the slurry will be converted to amino acids at relatively low first stage operating temperatures. Furthermore, the degree of amino acid deamination can be controlled by a judicious choice of first stage operating temperature, and as discussed hereinabove, addition of reagents such as sodium and sulfur.

As would be understood by one of ordinary skill in the art, the actual conditions under which the first stage reactor is run will vary according to the feedstock employed. For example, animal offal typically utilizes a first reaction temperature in the range about 200° C. to about 250° C. Municipal sewage sludge typically utilizes a first reaction temperature in the range about 170° C. to about 250° C.

The pressure in the first stage reactor is typically chosen to be close to the saturation pressure of the water at the operating temperature in question. The saturation pressure is the pressure that needs to be applied at a given temperature to keep the water from boiling, and also depends on the presence and quantity of other gases in the purified feed slurry. The total pressure in the reactor is greater than the vapor pressure of the water in the slurry mixture, so that the water does not boil off. The pressure is preferably in the range 45-55 atmospheres, may be in the range 40-60 atmospheres, and may also be in the range 30-70 atmospheres. Typically, the pressure is adjusted by amounts up to, and in the range of, 0-100 psi above saturation so that unwanted gases may be vented 336 from feed preparation, feed storage, or the first stage reactor.

One advantage of the present invention is that the venting during the feed preparation 110, feed storage 320, and first reaction permits gaseous impurities such as ammonia, carbon dioxide, and sulfur-containing gases to be removed. Typically, the first reaction 330 gives rise to sulfur-containing gases from the breakdown of sulfur-containing moieties in the various bio-materials. A principal source of sulfur is protein molecules, many of which have sulfur-bridges between cysteine residues. The sulfur-containing gases are typically hydrogen sulfide ($H_2S$), and mercaptans (alkyl-sulfur compounds) such as methyl mercaptan. Additionally, some salts such as calcium sulfide (CaS) may be produced, and these are normally separated during later stages.

After the first reaction, the reacted feed 122 that typically comprises at least one reacted liquid product and at least one reacted solid product and water, is flashed 340 to a lower pressure, and permitted to release excess heat back to the heating stages prior to the first reaction. Typically, flashing is achieved through multiple pressure reductions, preferably in two to three stages. The effect of flashing is to vent off remaining steam and gases 132 associated with the reacted feed. Dehydration via depressurization is efficient because water is driven off without using heat. The effective use of the excess heat is known as heat recovery, and represents a further advance of the process of the present invention. The fact that the first reaction uses water, which may be vented as steam, along with other gases 339, lends itself to efficient energy recovery. Water and steam are effective in heat exchange and may be redirected to the heating stages before the first reaction using one or more condensers. Condensers are quite compact and promote efficiency. Thus, steam and gases 132 vented from the reacted feed 122 are also preferably used to assist in heating the influent feed and in maintaining the temperature of the first reaction, thereby reducing the energy loss of the process of the present invention. Steam and gases 339 may also be passed to one or more heat exchangers placed prior to, or after, feed storage 320. Steam may also be directly injected back into the incoming feed 100 in some cases. Preferably, steam and gases 339 from first reaction 330 are combined with steam and gases 132 prior to passing to heat exchanger 114.

In the heat exchanger 114, the steam and gases are separated from one another. Most of the steam condenses to give a condensate 151. Preferably this condensate is redirected to combine with "produced water" that results from later stages of the process of the present invention, further described hereinbelow. Residual, small, amounts of steam are vented 116 along with the gases. Preferably these vented gases are combined with other gases that are produced by later stages of the process of the present invention to give fuel gas.

After the reacted feed has been flashed 340, and heat has been recovered, the intermediate feed 400 typically comprises at least one reacted liquid product, at least one reacted solid product, and water. The at least one reacted liquid product is typically a constituent of an organic liquor; the at least one reacted solid product typically comprises minerals. The intermediate feed preferably is substantially free of gaseous products.

Figure 4:
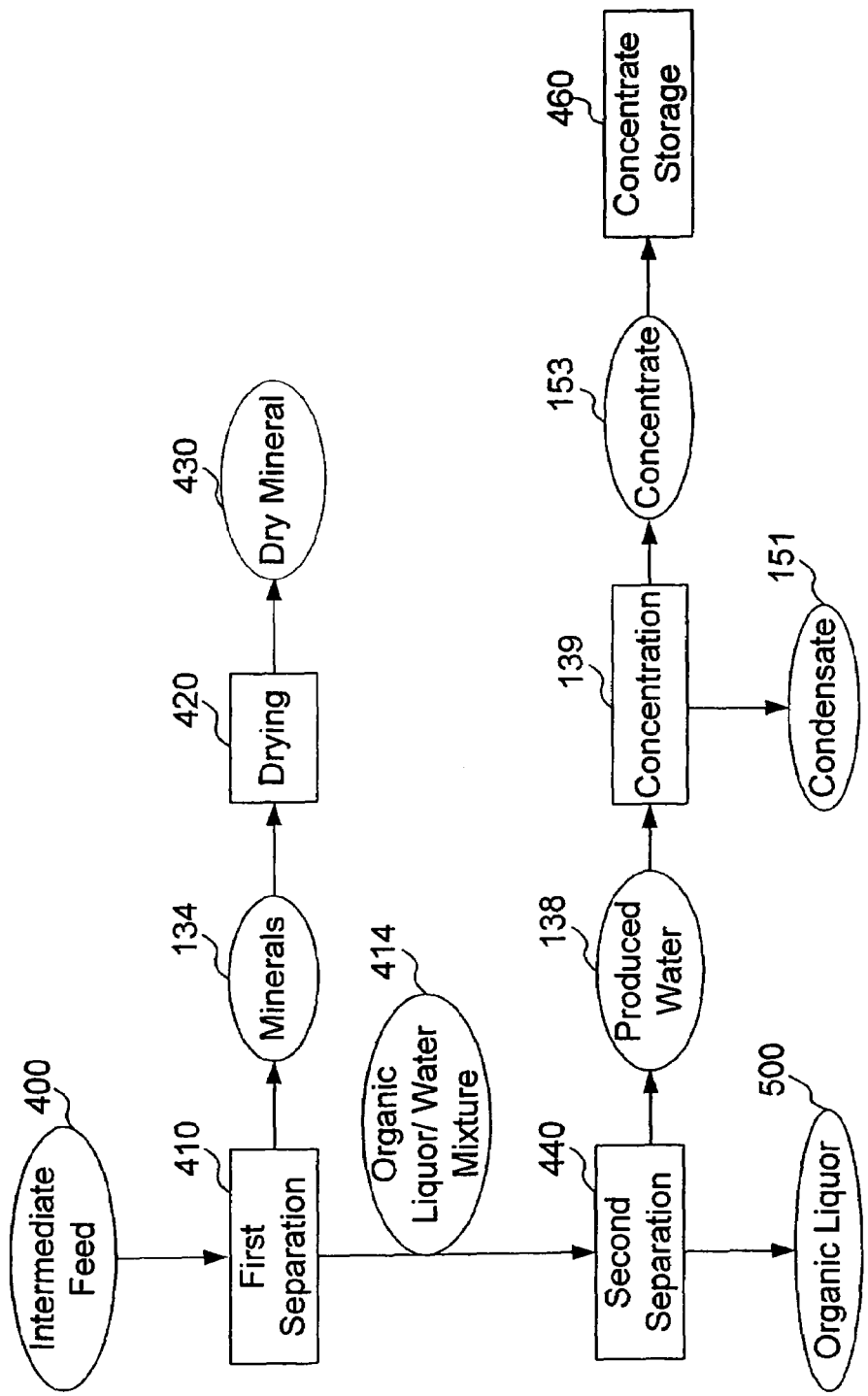
FIG. 4 shows a flow-chart of a second, separation stage of a process of the present invention.

FIG. 4 shows a sequence of separations that is applied to the intermediate feed. It is another advantage of the process of the present invention that the intermediate feed that results from the first reaction is subjected to one or more separation stages that removes minerals and water before processing in the third stage reaction. The separation stage uses separating equipment such as centrifuges, hydrocyclones, distillation columns, filtration devices, and screens, and may also use distillation to remove very fine carbon solids from an intermediate feed 400. In general, further pressure reduction recovers more steam, and facilitates solid/liquid separation to recover minerals and other solids.

Intermediate feed 400, typically comprising organic liquor, water, and minerals is preferably subject to a first separation 410 that removes most minerals 412 and produces a mixture of organic liquor and water 414 that is low in ash. Such a separation is characterized as a solid/liquid separation and may be achieved with a first centrifuge or via a solid/liquid separation device, for example by mechanical, or non-mechanical methods such as gravity settling. Minerals 412 that are separated out are typically wet and are thus subjected to a drying stage 420 before passing to a dry mineral storage 430. The drying stage typically takes place under normal atmospheric conditions. The resulting dry minerals may find considerable commercial application as a soil amendment or other industrial precursor.

The organic liquor/water mixture 414 is subject to a second separation 440 to drive off the water and leave the organic liquor 500. Such a second separation may be achieved using a second liquid/liquid centrifuge (or other separation device). Differences in gravity allow centrifugal separation of the produced water and organic liquor. The produced water 138 that is driven off contains small amounts of dissolved small organic molecules such as glycerol and some water soluble amino acids that derive from the breakdown of proteins. The produced water also typically includes chloride impurities. Separating out such impurities prior to the third stage reaction represents an additional benefit of the present invention because later products are thereby not contaminated.

The produced water 138 may be subject to concentration 139, such as by evaporation, producing a water condensate 151 that may be recycled within the process of the present invention, and a concentrate 153 that is dispatched to a concentrate storage 460. Evaporation is typically achieved by application of a slight vacuum. The concentrate, which largely comprises a slurry of amino acids, glycerol and, potentially ammonium salts such as ammonium sulfate or phosphate, will typically have commercial value as, for example, fertilizers known as "fish solubles" that are sold in domestic garden stores.

It is to be understood that the present invention is not limited to a separating stage comprising two steps. Nor is the present invention limited by the order in which any separation steps are carried out. Thus, it is consistent with the present invention if the separation of the intermediate feed 400 into products such as organic liquor, minerals, and water occurs in a single step or in more than two steps. Furthermore, minerals may, in some instances, be left in the organic feed by design, and their separation thus need not occur prior to third stage processing.

Figure 5:
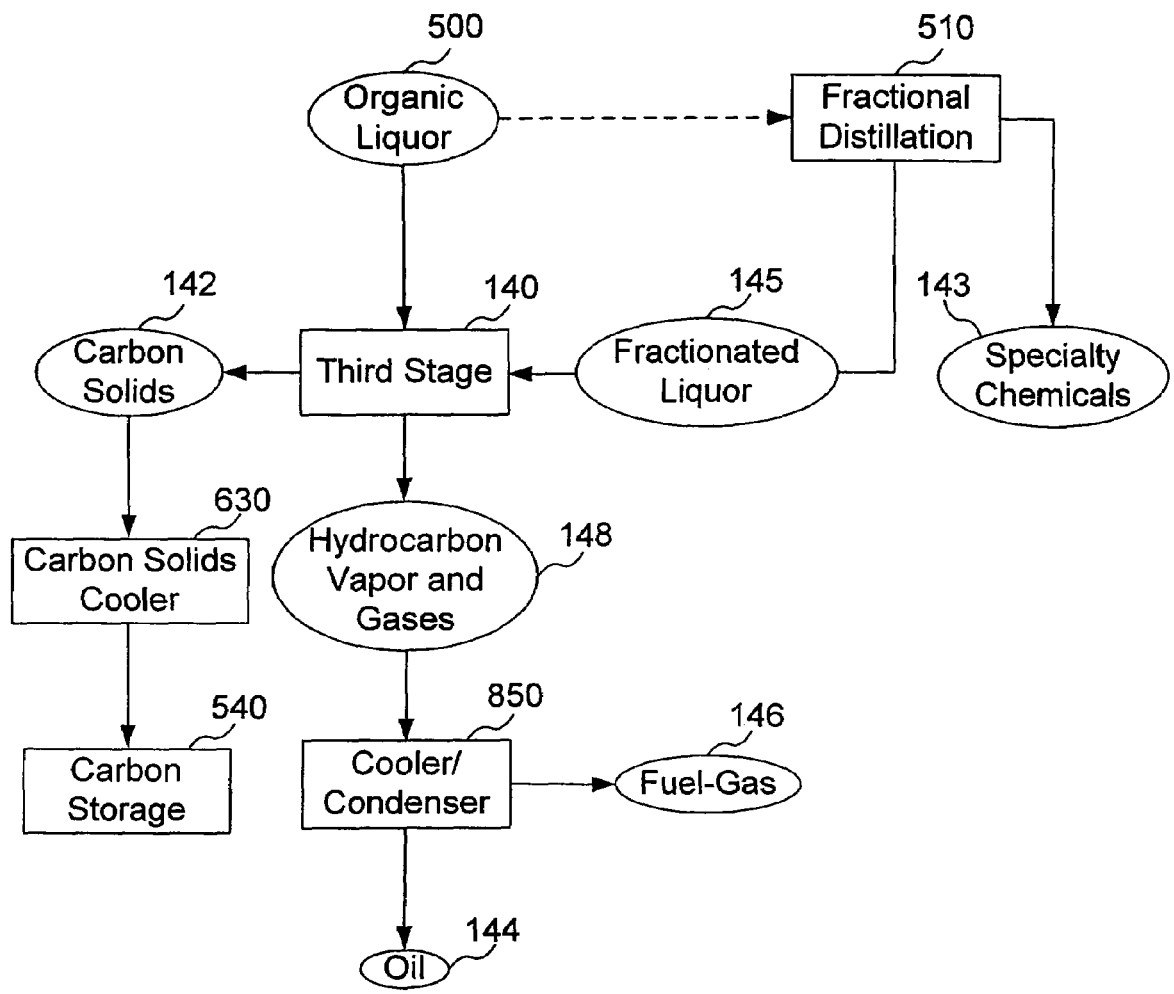
FIG. 5 shows a flow-chart of a third stage reaction of a process of the present invention.

FIG. 5 shows a stage of the process of the present invention wherein organic liquor 500 resulting from a separation stage of FIG. 4 is subject to a third stage 140 to produce one or more useful products. The organic liquor 500 ordinarily goes to a holding vessel before it is processed further.

A portion, or all, of organic liquor 500 can optionally be directed for processing ahead of the third stage 140 to yield one or more specialty chemicals 143. According to such an optional process, some desired portion of organic liquor 500 is typically subjected to a separation process such as fractional distillation 510 or reacted with a compound such as alcohol to form another compound, as would be understood by one of ordinary skill in the art. Such a separation process generates specialty chemicals 143, and leaves behind a fractionated liquor 145, often referred to as a "heavy liquor", that comprises higher molecular weight organic molecules such as triglyceride oils. Fractionated liquor 145 may be redirected to the third stage 140 for processing in a similar manner to organic liquor 500.

Specialty chemicals 143 are typically organic compounds such as fatty acids, fatty acid esters, fatty acid amides, or a range of amino acids. Preferably the specialty chemicals 143 are fatty acids. More preferably, specialty chemicals 143 are fatty acids in the range $C_{12-20}$. Even more preferably, the specialty chemicals 143 are fatty acids in the range $C_{16-20}$. When the specialty chemicals 143 are fatty acid amides and fatty acid esters, they are typically formed by reaction with fatty acids. The specialty chemicals 143 resulting from a feedstock such as turkey offal may find application as lubricants and coatings and paints.

In the third stage 140, the water content of the organic liquor 500 is almost zero, so that the conditions of the third stage are such that the remaining organic molecules are broken down largely by application of a high temperature, rather than by hydrolysis by excess, or added, water or steam. Typical conditions for carrying out the third stage are around 400° C., as may be obtained in a third stage reactor. The third stage typically takes from about 5 minutes to about 120 minutes. In practice, the various phases of the liquor spend varying amounts of time in the third stage reactor. For example, the vapors pass through relatively quickly, and the liquids take longer. The output from the third stage comprises, separately, a mixture of hydrocarbon vapor and gases 148 such as carbon dioxide, CO, and nitrogen and sulfur containing compounds, and carbon solids 142. The carbon solids 142 preferably resemble high quality coke. The mixture of hydrocarbon vapor and gases 148 typically contains oil vapor. The conditions of the third stage are preferably selected to optimize the purity of the carbon solids 142, and the mixture of hydrocarbon vapor and gases 148. Rapid quench of hot vapors, such as the mixture of hydrocarbon vapor and gases 148, stops reactions and minimizes carbon char formation after the third stage. In a preferred embodiment, rapid quenching of vapors may be achieved by directing the vapors into a drum full of water or by multiple quenching steps using thermal fluids and cooling mediums. Where such multiple quenching steps are employed, it is advantageous to take multiple cuts (diesel, gasoline, etc.) from the oil so that the various fractions can be diverted to separate commercial applications. Alternatively, in another embodiment, the oil vapor may be quenched in the presence of the incoming organic liquor, thereby also facilitating energy recovery.

Generally, the third stage is carried out at temperatures in the range of about 310° C. to about 510° C., so that at least one of the following two transformations can be carried out. First, fatty acids are broken down to hydrocarbons. This can be achieved by removing the carboxyl group from each fatty acid molecule at temperatures in the range approximately 316-400° C. Second, hydrocarbon molecules themselves are "cracked" to form a distribution of molecules of lower molecular weights, a process that can occur in the range approximately 450-510° C. Typically, however, hydrocarbon cracking occurs at temperatures above 480° C. Preferably, the third stage is carried out at a higher temperature than that for the first stage. It would be understood that the temperatures described herein applicable to the third stage could be varied without departing significantly from the principles of the present invention. For example, the third stage can be effectively carried out in the temperature range about 300-525° C., as well as in the range 400-600° C. In some embodiments, the temperature of the third stage reactor is between about 400° C. and about 510° C.

Furthermore, in at least one embodiment, the third stage reactor is slightly pressurized, to a pressure between about 15 psig and about 70 psig, i.e., from about 15 psi above atmospheric pressure, to about 70 psi above atmospheric pressure. Preferably the pressure in the third stage reactor is lower than that in the first stage reactor.

Carbon solids 142 generated from the third stage are typically first passed to a carbon solids cooler 630 wherein the carbon is permitted to lose its residual heat. After cooling, the carbon solids 142 are passed to carbon storage 540 and may be sold for a number of useful applications. For example, the carbon may be sold as a "soil amendment" for use in domestic horticulture because many of the bacteria in soil need a source of carbon. In particular, the carbon that is produced is of a quality similar to many forms of "activated carbon" and thus may also find application as a material for absorbing vapor emissions in automobiles, or for use in domestic water filters. Additionally the carbon, because of its level of purity, may find application as a solid fuel, like coal, but without the disadvantage of producing noxious emissions arising from combustion of the contaminants typically found in coal products. Also many environmental toxicants can be neutralized in a soil matrix by the use of a carbon additive like the carbon solids that results from the process of the present invention.

Instead of, or in addition to carbon solids 142, a useful product generated by the process of the present invention can be clean coal. Clean coal is generated when the raw feed is raw coal. It has been found that coal fines produced by the process of the present invention are advantageously freer of sulfur- and chlorine-containing contaminants than raw coal typically available. These properties of the coal generated by the process of the present invention makes them particularly attractive as sources of clean-burning fuel.

The mixture of hydrocarbon vapor and gases 148 produced by the third stage reactor is typically directed to a cooler/condenser 850 which separates the mixture into fuel-gas 146 and a hydrocarbon oil 144. The fuel-gas 146 has calorific value and may itself be redistributed internally within the process of the present invention for the purposes of providing energy for heating at various stages or can be used to produce electrical or other forms of energy for external or internal use. The oil 144 typically comprises hydrocarbons whose carbon chains have 20 or fewer carbon atoms. In this respect the mixture resembles the lighter components of a fuel-oil such as a #2 grade diesel oil. Such a product is also commercially saleable. It is to be understood, however, that the precise composition of the oil 144 depends upon the feedstock. Thus the composition of the oil obtained when the feedstock is composed of tires is different from the composition when the feedstock is turkey offal. It has been found that the oil resulting from feedstocks that have a high fat content is rich in olefins, and di-olefins. If not desired, such olefins may be removed from the oil by resaturation or separation methods.

When the raw feed is municipal sewage sludge, it is preferable to facilitate the separation of the organic from the inorganic materials. Accordingly, in a preferred embodiment, some of the hydrocarbon oil 144, in this case bio-derived hydrocarbons, are redirected to the raw feed or the product of the first reaction, in order to assist with floating the material. In other embodiments, materials such as trap grease, as are obtained from fast food outlets for example, can be used. The principle behind floating the material is that a material that is lighter than water is introduced to the raw feed, or the product of the first reaction, to assist with floating the heavier than water organic materials, thereby facilitating the separation of organic from inorganic materials. The result is a sludge that is easier to centrifuge than would otherwise be the case.

A further advantage of the process of the present invention is that all of the products are DNA and pathogen-free. That is, they are free of pathological materials that are derived from animal cells, bacteria, viruses, or prions. Such materials do not survive the process of the present invention intact. This is an important outcome because there is no risk of using any of the products of the process of the present invention in agricultural applications where there would be a danger that such molecules could re-enter the food-chain.

Figure 6:
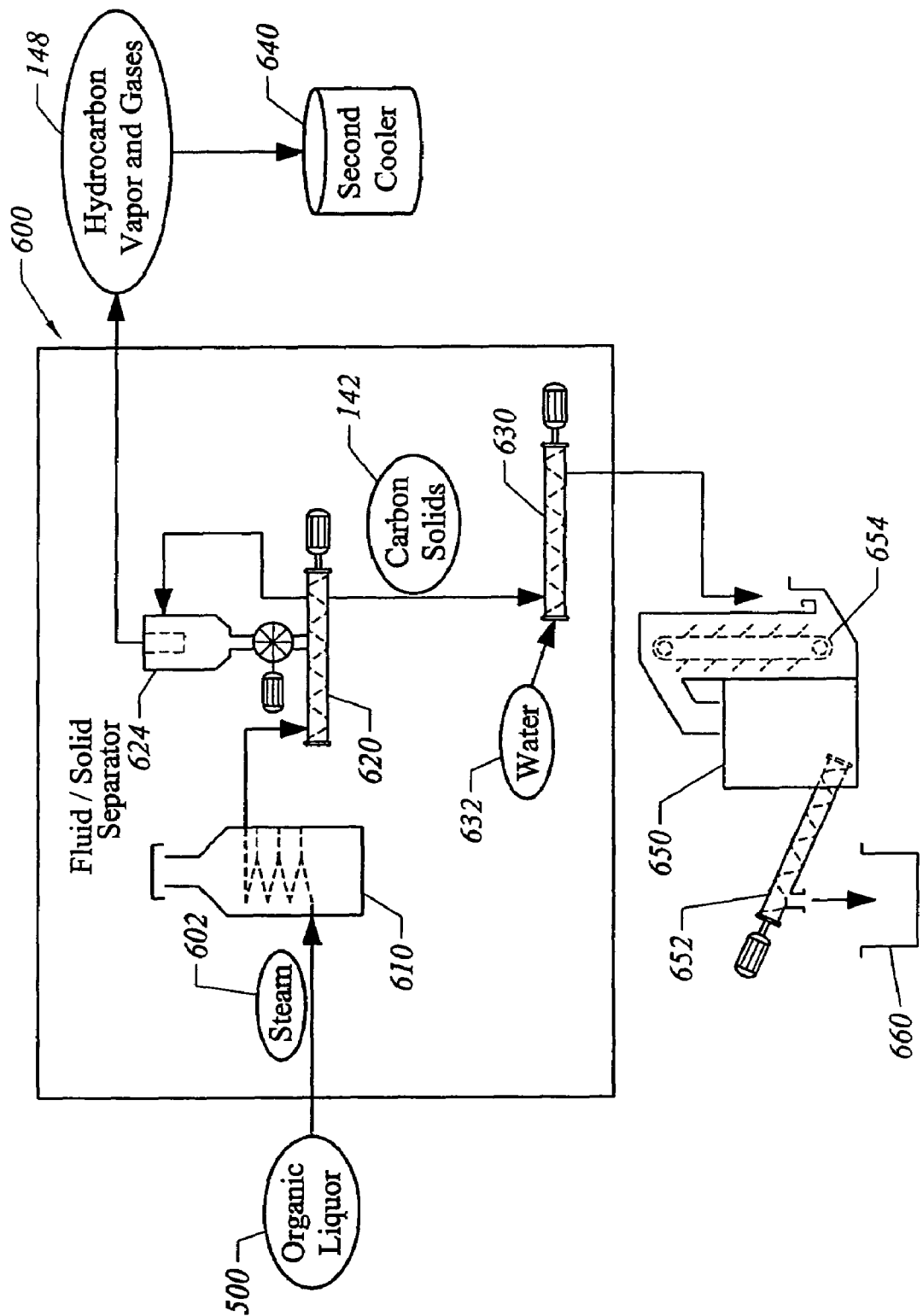
FIG. 6 shows an apparatus for carrying out a third stage of the process of the present invention.

An apparatus for converting reacted liquid product from the separation stage, such as an organic liquor, into a mixture of hydrocarbons, and carbon solids, is a suitable third stage reactor for use with the process of the present invention. As shown in FIG. 6, a third stage reactor 600 according to an embodiment of the present invention comprises a heater 610 for heating the organic liquor, thereby producing a mixture of liquid and vaporized oil; a reactor 620 for converting the mixture of liquid and vaporized oil into carbon solids 142, and a mixture of hydrocarbon vapor and gases 148; a first cooler 630 for accepting the carbon solids 142; and a second cooler 640 for accepting the hydrocarbon vapor and gases. Third stage reactor 600 may additionally comprise a fluid-solid separator 624 communicating with reactor 620 for separating hydrocarbon vapor and gases 148 from carbon solids 142.

The heater 610 is preferably efficient and compact, comprising a large number of internal tubes that give rise to a large surface area for heat exchange. The heater 610 is typically a "fired heater". Heater 610 typically has an inlet for accepting organic liquor and steam 602, and an outlet for directing heated organic liquor/steam mixture to reactor 620. Steam 602 in an amount approximately 2-5% by weight accompanies the organic liquor as it enters heater 610. Such a quantity of steam helps uniform heating and prevents residue build-up on the inside of the heater. In a preferred embodiment, one or more pre-heaters are used to heat organic liquor 500 prior to mixing it with steam and/or transferring it to heater 610. Pressure for the third stage is imparted by a pump system after storage 500.

Reactor 620 preferably comprises at least one heated auger, and has and inlet and an outlet configured, respectively, to accept a heated mixture of liquid and vaporized oil from heater 610, and to direct carbon solids and a mixture of hydrocarbons and gases into a fluid-solid separator. The heated mixture of liquid and vaporized oil with steam is passed into the reactor 620 where it splits into carbon solids, and a mixture of hydrocarbon gases that preferably contains constituents of oil and fuel gas. Typically, the carbon solids produced amount to about 10% by weight of the mixture of liquid and vaporized oil. In other embodiments, depending upon the constituents of the raw feedstock, the carbon solids produced are between about 5% and about 20% by weight of the mixture of liquid and vaporized oil. In some embodiments of the present invention, to avoid build up of excess carbon solids in reactor 620, the amount of feedstock processed is adjusted.

An auger is suitable for producing carbon solids and a mixture of hydrocarbons because it permits control of residence time and temperature of the incoming organic liquor, and because it permits efficient separation of the carbon solids and the volatile products. Preferably the dimensions of the auger are selected so that the purity of the resulting hydrocarbon mixture and the carbon solids is optimized. For example, the cross-sectional diameter of the auger principally determines the rate of flow of vapors through it. Preferably the rate of flow is not so high that dust is carried through with the vapors to produce an impure hydrocarbon mixture. The residence time of the heated mixture of organic liquor, vapors and steam, as it reacts, also determines the size of the auger.

Preferably the third stage reactor 600 includes a fluid-solid separator that communicates with the outlet of the reactor 620. The fluid-solid separator preferably has a first outlet for hydrocarbons and gases, and a second outlet for carbon solids. Some of the fuel gas from the mixture of hydrocarbons and gases is preferably redirected back to heater 610 and burned to help maintain the temperature in the heater, thereby promoting overall efficiency of the process of the present invention.

The carbon solids—often at a temperature as high as about 500° C.—are directed into a first cooler, carbon solids cooler 630, which is preferably a cooling auger which communicates with the reactor through an air lock device, or optionally the fluid-solid separator. In some embodiments of the present invention, more than one cooling auger 630 may be employed. It is preferable to introduce water 632 into carbon solids cooler 630 to assist with the cooling process. The carbon solids are transferred to a finished product storage system 650, optionally via a transfer auger or some other conveyancing device such as a bucket elevator 654 or to another heater/reactor to activate the carbon solids.

The second cooler 640 for accepting the mixture of hydrocarbon vapor and gases preferably comprises a carbon particulate separator for separating out any residual carbon solids and returning them to reactor 620.

A modified version of the process of the present invention could be used to inject steam into underground tar-sands deposits and then refine the deposits into light oils at the surface, making this abundant, difficult-to-access resource far more available. Experiments also indicate that the process of the present invention can extract sulfur, mercury, naptha and olefins—all saleable commodities—from coal, thereby making the coal burn hotter and cleaner. Pre-treating via the process of the present invention also makes some coals more friable, so less energy is needed to crush them prior to combustion in electricity-generating plants.

For some feedstocks, the process of the present invention employs a device for separating fine suspended solids from a fluid as part of the feed preparation stage. For example, Municipal Sewage Sludge typically contains 300 ppm solids and is therefore too dilute to process efficiently with the methods of the present invention without prior concentration. Accordingly it is preferable to employ a separator to remove water from a weak slurry such as MSS by filtering out the particles. The particles are then captured accompanied by some water in a more concentrated slurry (having a particulate concentration in the range 10,000 ppm to 500,000 ppm) and discharges surplus water. The concentrated slurry then becomes the feedstock that is used with the process of the present invention.

Figure 7:
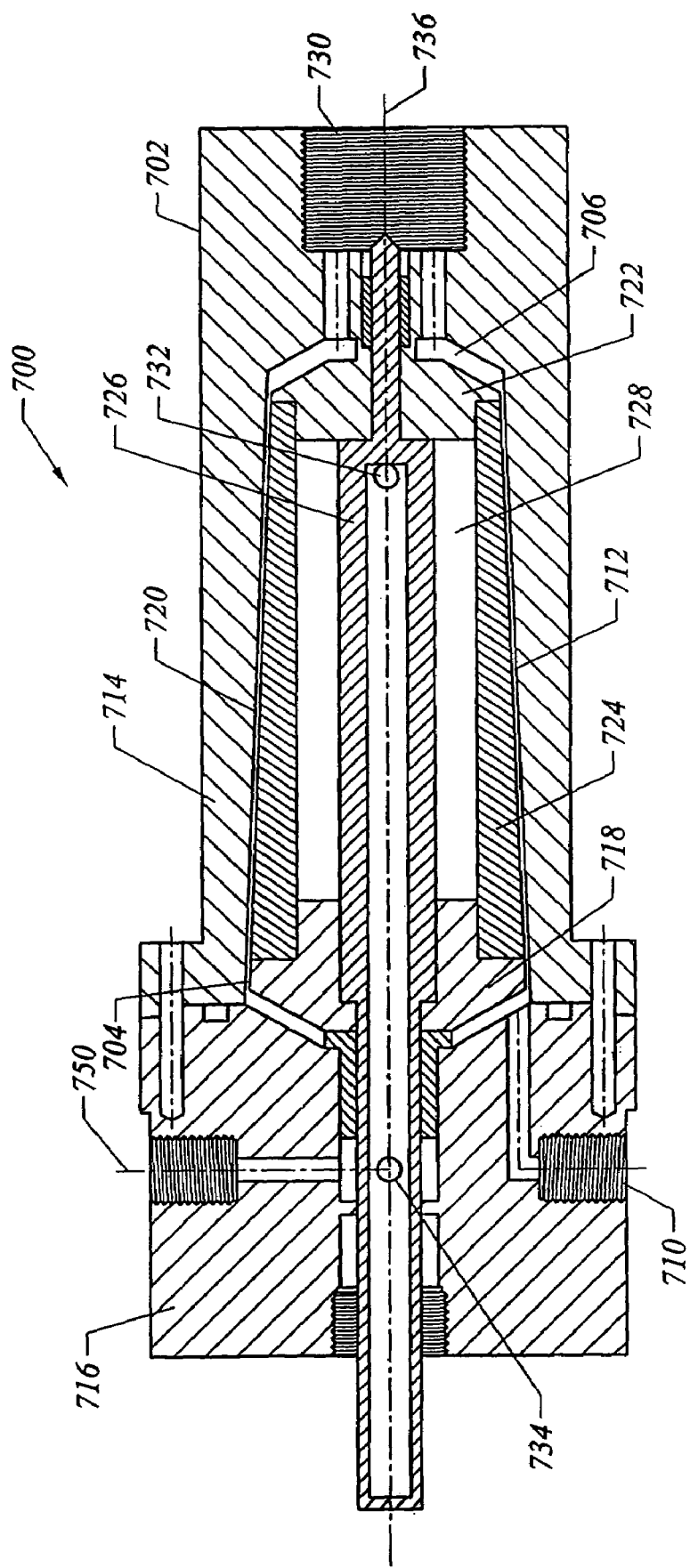
FIG. 7 shows an apparatus for separating fine suspended solids from a fluid.

In addition, many other industrial and commercial applications require suspended solids to be separated from a liquid. FIG. 7 illustrates a separating device 700 according to a preferred embodiment of the invention that is useful for such separations. Another example of an application requiring the separation of a solid suspension is the separation of red and white blood cells from whole blood. When the size of the suspended solid particles is large, or their density is significantly different from that of the fluid, there are many different types of apparatus that can separate them. For example, filters of many different configurations with openings smaller than the suspended solid particles can be used for solid material that does not deform significantly under strain. Clarifiers, settling chambers, and simple cyclones can be used effectively when there is a significant density difference between the solid particles and the fluid. As the size or density difference become smaller, active devices using centrifugal forces can be effective. However, the efficiency of all these separating devices decreases dramatically for very small particle sizes with deformable material that has a density only slightly different from that of the suspending fluid.

With respect to a preferred process of the present invention, one application where the suspended solids are small, deformable, and have small density difference is municipal sewage sludge (MSS). The suspended material in MSS consists primarily of cellular material and cellular debris from bacteria and typically has dimensions of about 1 micrometer. This material is deformable and has an effective density within 10% of that of the suspending water medium. Separating this solid material from water is a preferred step in preparing MSS as a feedstock for the process of the present invention. Such separation may be achieved through use of centrifuges; however, in a preferred embodiment, separating device 700 is employed.

According to a preferred embodiment of the present invention, it is preferable to employ separating device 700, as illustrated in FIG. 7, for separating solid and liquid components of a raw feed such as MSS, prior to further processing by the methods of the present invention. Such a device may also be applied to other industrial or commercial wastewater sludges whose solid particulates are deformable, or whose effective density is within about 10% of that of the liquid phase.

Device 700 preferably comprises a housing 702 that contains a spinning assembly 704 mounted in an inner chamber 706 having a frusto-conical shape. The shape of inner chamber 706 typically comprises a frusto-conical section that has an angle of taper, with additional sections at the base and/or at the top of the frustum that house other parts of spinning assembly 704. The housing 702 preferably comprises a spinner case bottom 714 and a spinner case top 716 that are joined to one another, and that enclose the spinning assembly 704. Separating device 700 further comprises an inlet 710 and a first outlet 730 that communicate with the inner chamber, and a second outlet 750. Inlet 710 permits introduction of the fluid that contains the suspended solids into an annular space 712 between a stationary inner wall 720 of the inner chamber, and the spinning assembly.

The spinning assembly comprises a frusto-conically shaped cylinder with a hollow interior, which is preferably made from a spinner bottom 722, connected to a tapered cylindrical wall 724 which itself is connected to a spinner top 718. The spinning assembly is concentrically mounted on a longitudinal axis 736 of a hollow spindle 726 which rotates at speeds typically in the range about 1,000 r.p.m. to about 50,000 r.p.m. In a preferred embodiment for separation of MSS, the rotation speed is about 10,000 r.p.m. Preferably the rotation speed is chosen so as to minimize chaotic flow. The spinning assembly is tapered so that the effective cross-sectional area decreases as the width narrows. Typically the angle of taper is between about 1° and about 10°. In a preferred embodiment, the angle of taper is between about 2° and about 2.5°, and is even more preferably about 2.25°. The hollow interior of the spinning assembly communicates with a second outlet 750.

Preferably there is a pressure differential between the inlet 710 and the interior of the separator device 700. Typically, this pressure differential is between about 3-150 p.s.i. and is controlled by two pumps (not shown in FIG. 7).

The flow rate for different sized separators will scale with the surface area of the rotating cylinder. Preferably, the inlet and the annular gap are configured to provide a flow rate between about 1 and about 200 gallons per minute. More preferably, the flow rate is between about 1 and about 20 gallons per minute. Even more preferably for handling MSS, the flow rate is about 10 gallons per minute.

The wall 724 of the spinning assembly is perforated. The pore size in the wall 724 is typically between about 1 and about 200 micrometers. Preferably, the pore size is about 50 micrometers. The wall 724 is preferably made of a plastic material such as HDPE or any other material that is not hygroscopic, to avoid closure of the pores during operation.

The fluid and suspended material flow along the annular passage 712 in a generally axial direction while a portion of the fluid flows through the perforated rotating wall 724 into the hollow interior 728 of the cylinder. Hollow interior 728 communicates with hollow spindle 726 through spindle inlet 732. Most of the suspended particles are prevented from flowing with the fluid through the perforated cylinder due to shear and centrifugal forces at the surface of the rotating cylinder. The rotational speed of the cylinder effectively sets the shear and centrifugal forces on the suspended particles, and so can be used to control the minimum size of the particle that can be prevented from following the fluid through the perforated cylinder. The water and particles that flow into the interior of the cylinder 728 subsequently flow through spindle inlet 732 into the center of hollow spindle 726, and flow towards spindle outlet 734 before being discharged through a second outlet 750.

The material in the annular passage 712 follows a tight spiral flow path in response to the motion of the rotating cylinder. Preferably the thickness of annular passage 712 is constant along its length. For some applications this annular space may vary from top to bottom. Variations in annular space can impart flow conditions near the perforated spinner surface. A first outlet 730 for discharging the now concentrated fluid stream is provided at the end of the annular passage away from the entrance.

The operation of the device of FIG. 7 is preferably orientation-independent. In a preferred embodiment, the axis of the tapered cylinder is oriented vertically with the first outlet 730 at the bottom.

An advantage of the device of FIG. 7 over other separation devices known in the art is that it can process sludges with a wide range of particle characteristics, in particular including those with deformable suspended solids in the size range below 1 micrometer or those that have densities within 10% of the suspending fluid. In a preferred embodiment, the annular gap and the pore size in wall 724 are configured for separating a suspension of municipal sewage sludge. In some embodiments of the process of the present invention, many such separators are used, in parallel, to achieve high throughput separation of a raw feedstock.

It is to be understood that the separator 700 depicted in FIG. 7 is not drawn precisely to scale, though the various elements are in approximate proportion to one another. Thus, separator 700 may be constructed according to ordinary principles familiar to one of ordinary skill in the art of mechanical engineering and design.

In a preferred embodiment, the outer diameter of spinner bottom 722 is about 2", and the outer diameter of the spinner top 718 is about 2.2". The preferred length of spinner case bottom 714 is between about 7" and about 8". The preferred length of spinner wall 724 is between about 4" and about 6", and its preferred thickness is preferably constant along its length and is about 1.5". The preferred diameter of outlet 730 in conjunction with such a spinner is about 0.8" and the outer diameter of the spinner case bottom is preferably about 3". The outer diameter of spinner case top is then preferably about 4". Spindle 726 is hollow and preferably has an inside diameter of about 0.25". The outside diameter of spindle 726 may vary along its length and may be between about 0.5" and about 0.75". The distance between spindle inlet 732 and spindle outlet 734 may be about 6" in such an embodiment. The thickness of annular passage 712 is preferably about 0.05 to about 0.50 inches.

The preferred dimensions presented herein are to be taken as but one illustration, and, according to design choice and desired throughput, a mechanical engineer of ordinary skill in the art would be able to scale up or down the size of the various elements of separator 700 in order to achieve operating efficiency.

The overall apparatus for carrying out the process of the present invention is preferably accompanied by a computerized control system that comprises simple controllers for valves, pumps, and temperatures. Development of such a system is within the capability of one of ordinary skill in the art of computer process control engineering.

The apparatus of the present invention may be scaled according to need. For example, plants that handle many thousands of tons of waste per day can be envisioned, whereas portable plants that could be transported on the back of a flatbed truck and that might only handle one ton of waste per day can also be built.

EXAMPLES

Example 1

Pilot Plant

A pilot plant has been built employing apparatus and processes of the present invention. The pilot plant can handle approximately seven tons of waste per day.

According to one exemplary application of the pilot plant, the experimental feedstock was turkey processing-plant waste: feathers, bones, skin, blood, fat, viscera. An amount of 10,044 pounds of this material was put into the apparatus's first stage: a 350-horsepower grinder, which turns the material into gray-brown slurry. From there, the material flowed into a series of tanks and pipes which heated and reformed the mixture.

Two hours later, a light-brown stream of steaming fine oil was produced. The oil produced by this process is very light. The longest carbon chains are $C_{20}$. The produced oil is similar to a mix of half fuel oil, half gasoline.

The process of the present invention has proved to be 85% energy efficient for complex feedstocks such as turkey offal. This means that for every 100 B.t.u. (British thermal units) in the feedstock entering the plant, only 15 B.t.u. are used to run the process. The efficiency is even better for relatively dry materials, such as carbon-heavy or moisture-light raw materials such as plastics.

The first stage reactor, comprises a tank approximately 20 feet tall, three feet wide, and heavily insulated and wrapped with electric-heating coils. In the first stage reactor, feedstock is hydrolyzed by means of heat and pressure. Both temperatures and pressures are not very extreme or energy-intensive to produce because water assists in conveying heat into the feedstock. It usually takes only about 15 minutes for this process to occur in the pilot plant.

After the organic materials are heated and partially depolymerized in the reactor vessel, a second stage begins. In this phase, the slurry is dropped to a lower pressure. The rapid depressurization instantly releases about half of the slurry's free water. Dehydration via depressurization is far more efficient than heating and boiling off the water, particularly because no heat is wasted. Water that is "flashed-off" is sent up a pipe that leads back to the beginning of the process to heat the incoming process stream.

In this second stage, the minerals settle out, and get shunted to storage tanks. In turkey waste, these minerals come mostly from bones. The minerals come out as a dried brown-colored powder that is rich in calcium and phosphorous. It can be used as a fertilizer because it is well-balanced in micro-nutrients. In particular it has a useful range of micro- and macro-nutrients. The minerals contain the correct amounts of elements such as calcium and phosphorous required for healthy plant growth and development.

In the pilot plant, the remaining concentrated organic materials flow into a third stage reactor and is subjected to third stage processing, as described hereinabove. Gases resulting from the processing were used on-site in the plant to heat the process of the present invention. The oil and carbon flow into storage as useful higher value products.

Depending on the feedstock and the first and third stage processing times, the process of the present invention can make other specialty chemicals, which are extracted at various sections of the process. Turkey offal, for example, can make fatty acids for use in soap, tires, paints and lubricants.

Example 2

Operating Plant

A full-sized commercial-scale installation is under construction, intended to process over 200 tons of turkey-waste daily. The plant is designed to produce about 10 tons of gas per day, which returns to the system to generate heat to power the system. The plant will produce about 21,000 gallons of water, which is clean enough to discharge into a municipal sewage system, and is also free of pathological vectors. The plant also will make about 25 tons of minerals, concentrate and carbon, and about 500 barrels of high-quality oil of the same grade as a #2 heating oil.

Example 3

Exemplary Conversions of Waste Products

Table 1 shows end-products, and their proportions, for 100 lbs of each of the following waste product, when they are converted to useful materials using the process of the present invention: Municipal Sewage Waste (comprising 75% sewage sludge and 25% grease-trap waste); Poultry Processing Waste (comprising organs, bones, blood, feathers and fat); Paper; and Heavy Oil (such as refinery-vacuum residues and tar sands). Amounts in Table 1 are in pounds.

TABLE 1

| Feedstock | Oil | Gas | Solids & Concentrate | Water |
|---|---|---|---|---|
| Municipal Sewage Sludge | 26 | 9 | 8 (carbon and mineral solids) † | 57 |
| Poultry Processing Waste | 39 | 6 | 5 (carbon and mineral solids) | 50 |
| Paper ‡ | 8 | 48 | 24 (carbon solids) | 20 |
| Heavy Oil | 74 | 17 | 9 (carbon solids). | — |

‡ For paper, the figures are based on pure cellulose; it is estimated that yields for specific paper feedstocks such as newspapers or office waste paper would be within 10 % of these figures.
† The solid output from municipal sewage sludge may also contain heavy metals.

It is worth noting that the yields from cattle and pork processing wastes are similar to those from poultry processing waste.

Example 4

A Bio-derived Oil

A bio-derived oil can be produced from a wide range of organic materials using the process of the present invention. One such bio-derived oil comes from turkey offal, comprises C-20 and shorter carbon-chain components, and virtually eliminates particulate emissions when used as a fuel. This oil provides refineries or blenders with a narrow range 40-plus American Petroleum Institute (API) renewable oil that can be used as an alternative fuel, or a blending component for combustible fuels. Salient properties of this oil are shown in Table 2, wherein the specification methods are designated by an ASTM (American Society for Testing Materials) code.

TABLE 2

| Fuel Property | Specification Method | Bio-derived Oil |
|---|---|---|
| API Gravity at 60° F. | D-287 | 40+ |
| Flash Point (° F.) | D-93 | 100 |
| Distillation, Recovery, ° F. (Typical) | D-86 | |
| Initial Boiling Point, ° F. | | 125 |
| 10% | | 160 |
| 20% | | 220 |
| 30% | | 280 |
| 40% | | 335 |
| 50% | | 400 |
| 60% | | 450 |
| 70% | | 500 |
| 80% | | 580 |
| 90% | | 660 |
| Recover, Vol. % | | 95% |

TABLE 2-continued

| Fuel Property | Specification Method | Bio-derived Oil |
|---|---|---|
| Appearance | D-4176 | Clear and Bright |
| Cloud Point ° C. | D-2500 | −10 |
| Pour Point ° C. | D-97 | −20 |
| Viscosity @ 40° C., cSt | D-445 | ~1.50 |
| Sulfur, Wt. % | D-4294 | <0.15 |
| Copper Corrosion Rating (2 hrs @ 212° F.) | D-130 | <2 |
| Cetane Index | D-976 | ~40 |
| BS&W (Basic Sediment and water), Vol. % | D-2709 | <0.10 |
| Ash, Wt. % | D-482 | <0.005 |
| Carbon Residue, Wt. % | D-524 | <0.50 |
| Heat Content, BTU/lb | D-240 | ~18,800 |
| PONA, Wt. % (Typical) | D-5443 | |
| Paraffins | | 22 |
| Olefins | | 14 |
| Naphthenes | | 3 |
| Aromatics | | 6 |
| C-14/C-14+ | | 55 |

In Table 2, the weight percent of paraffins, olefins, naphthenes, and aromatics refer to molecules that contain up to and including 13 carbon atoms.

Example 5

Embodiment of a Third Stage Reactor and Cooler/Condenser

Figure 8A:
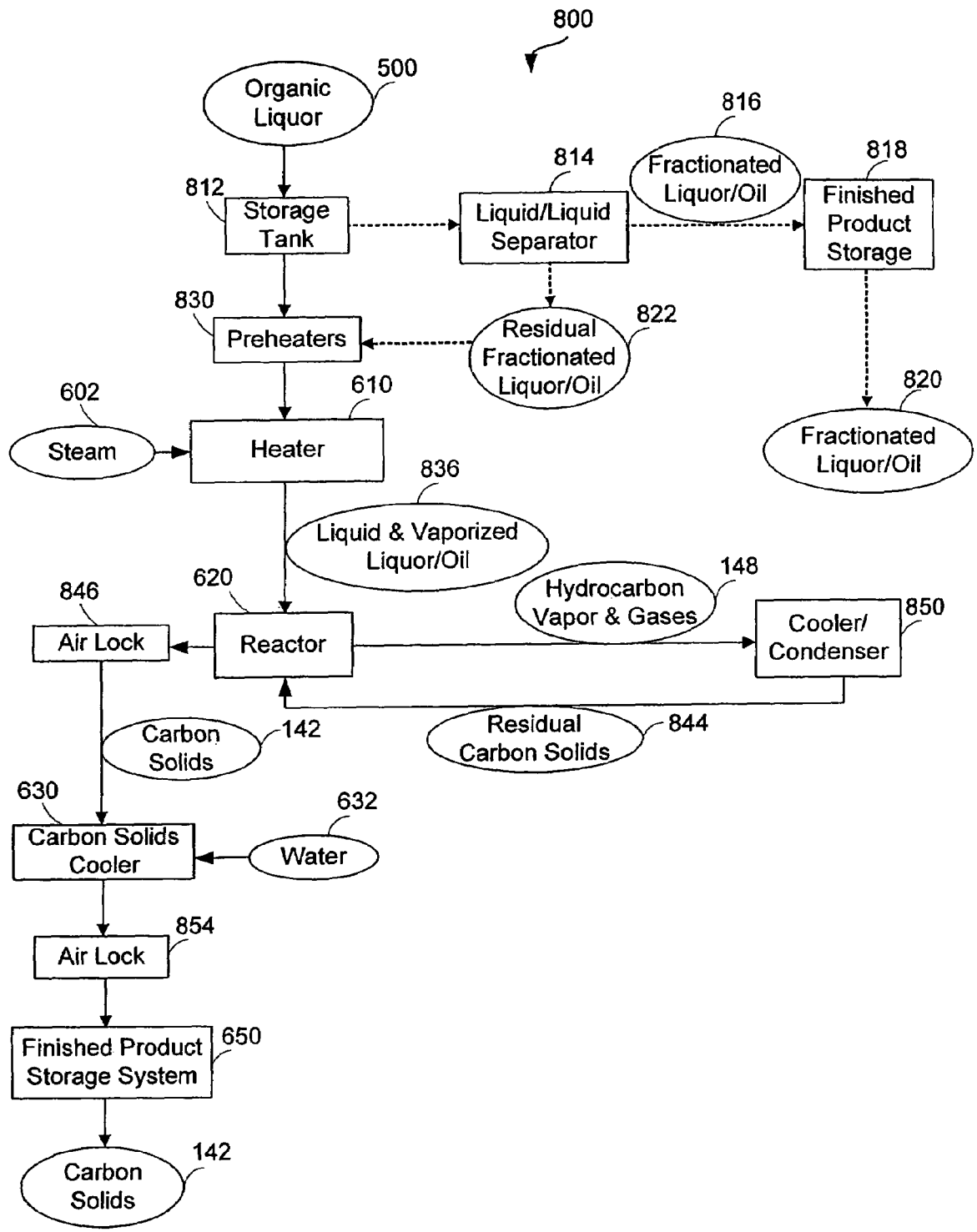

FIGS. 8A and 8B show an embodiment of an apparatus for use with the process of the present invention. Some elements are also shown in FIG. 6.

FIG. 8A shows an apparatus for use with the third stage of the process of the present invention. Organic liquor 500 passes into a storage tank 812. Optionally, organic liquor and oil may be directed to a liquid/liquid separator 814 and divided into a first portion of fractionated liquor/oil 816 and a second portion of, or residual, fractionated liquor/oil 822. The first portion of fractionated liquor/oil may be directed to finished product storage 818, and distributed as fractionated liquor/oil 820 which can be recycled or sold. The second portion of fractionated liquor/oil 822 is redirected to one or more preheaters 830.

Having been heated, the fractionated liquor/oil 822, or the unseparated liquor/oil 500 is passed to a heater 610, preferably accompanied by steam 602. Resulting liquid and vaporized liquor/oil 836 is passed to a reactor 620, such as an auger, and separated into hydrocarbon vapor and gases 148, and carbon solids 142. The hydrocarbon vapor and gases 148 are passed to a cooler/condenser 850, which is further described in FIG. 8B. Any remaining particulates in the oil vapor and gases, such as residual carbon solids 844, are removed and returned to the reactor 620.

Carbon solids 142 are directed through an air lock 846, and into a carbon solids cooler 630, wherein they are mixed with water 632. The resulting mixture of water and carbon solids is passed through another air lock 854 into a finished product storage system 650. Final product carbon solids 142 may be distributed to one or more commercial applications.

For use in conjunction with apparatus 800 shown in FIG. 8A, is a cooler/condenser 850, shown in FIG. 8B. Cooler/condenser 850 facilitates a number of separation cycles wherein a mixture of oil vapor and gases, which may also contain water and particulates, is subject to a number of different separation steps. Hydrocarbon vapor and gases 148 from reactor 620 pass into a carbon particulate separator 842, which separates out remaining solid particles, such as residual carbon solids 844, and redirects such solids back to reactor 620.

The hydrocarbon vapor and gases that emerge from the carbon particulate separator pass into a vapor quenching system 860, implemented according to general principles that would be understood by one of ordinary skill in the art. From the vapor quenching system, oil and gases 870 pass into an oil/water/gas separator 872 which further separates the various components such as oil 862, slop oil 876, gas and LPG 874, and an oil/carbon slurry 881.

Oil 862 passes to a heat exchanger 864 and thereafter into a finished product storage system 866, and is sold as oil 144.

Gas and liquid petroleum gas ("LPG") 874 pass into a condenser 890 which separates out LPG 898 from the other gaseous components. Gas 894 is passed to super heater 892 to yield a fuel gas 146, which can be delivered to one or more devices as a source of energy. LPG 898 is recycled in the following way. First, LPG 898 is passed through a liquid/solid separator 884, and any residual carbon solids 886 are removed. Then, the separated LPG, mixed with oil separated from the oil/carbon slurry 881, is returned to the oil/water/gas separator 872, and a further separation takes place. The cycle wherein the gas and LPG mixture is separated and condensed may be repeated as many times as is desired.

An oil/solid mixture, typically an oil/carbon slurry 881, may also be directed from oil/water/gas separator 872 to liquid/solid separator 884 in order to remove residual carbon solids 886. The separated oil, mixed with LPG, is preferably returned to the oil/water/gas separator for further redirection, as appropriate.

Slop oil 876 from oil/water/gas separator 872 is passed to an oil/water separator 878, and water 880 is released, or may be recycled. Oil 882 from the oil/water separator is passed back to the oil/water/gas separator for further iterations of the separation cycle.

The foregoing description is intended to illustrate various aspects of the present invention. It is not intended that the examples presented herein limit the scope of the present invention. The invention now being fully described, it will be apparent to one of ordinary skill in the art that many changes and modifications can be made thereto without departing from the spirit or scope of the appended claims.

What is claimed:

1. A process for converting a feedstock into at least one useful material, wherein the feedstock contains carbohydrates and proteins, comprising:
   preparing a slurry from the feedstock;
   reacting the slurry in a first reaction to produce a reacted feed comprising at least one reacted solid product, at least one reacted liquid product, and water, wherein said first reaction includes addition of one or more reagents that suppress hydrolysis of carbohydrates, and encourage dissociation of amines;
   separating said at least one reacted solid product, said water, and said at least one reacted liquid product from said reacted feed; and
   converting said at least one reacted liquid product into at least one useful material in a second reaction.

2. The process of claim 1 wherein said at least one useful material is carbon solids.

3. The process of claim 1 wherein said at least one useful material comprises a mixture of hydrocarbons.

4. The process of claim 3 wherein said mixture of hydrocarbons comprises a fuel gas and an oil.

5. The process of claim 1 wherein said preparing comprises driving off ammonia from said feedstock.

6. The process of claim 1 wherein said first reaction takes place at a pressure of about 20-120 atmospheres.

7. The process of claim 6 wherein said pressure is about 50 atmospheres.

8. The process of claim 1 wherein said first reaction takes place at a temperature in the range about 150° C. to about 330° C.

9. The process of claim 1 wherein said one or more reagents is sodium.

10. The process of claim 1 wherein said one or more reagents is sulfur.

11. The process of claim 1 wherein said one or more reagents creates reducing conditions appropriate for liberation of ammonia.

12. The process of claim 1 wherein said one or more reagents creates $H_2SO_4$ in situ.

13. The process of claim 1 wherein said reacting drives off at least one contaminant.

14. The process of claim 13 wherein said at least one contaminant is a sulfur-containing material.

15. The process of claim 13 wherein said at least one contaminant is a mercury-containing material.

16. The process of claim 13 wherein said at least one contaminant is a halogen-containing compound.

17. The process of claim 1 wherein said reacting drives off steam.

18. The process of claim 17 wherein said steam is redirected to heat said slurry during said preparing.

19. The process of claim 1 wherein said separating comprises a first separation and a second separation.

20. The process of claim 1 wherein said at least one liquid product comprises at least one fat derivative or fatty acid.

21. The process of claim 1 wherein said at least one solid product comprises at least one mineral compound.

22. The process of claim 1 wherein said feedstock comprises municipal sewage sludge.

23. The process of claim 1 wherein said feedstock is selected from the group consisting of: leaves, grass clippings, bagasse, seaweed, cotton waste, and animal waste.

24. A process for converting turkey offal into at least one useful material, wherein the turkey offal contains carbohydrates and proteins, comprising:

preparing a slurry from the turkey offal;

reacting the slurry in a first reaction to produce a reacted feed comprising at least one reacted solid product, and at least one reacted liquid product, and water, and wherein said first reaction includes addition of one or more reagents that suppress hydrolysis of carbohydrates, and encourage dissociation of amines;

separating the at least one reacted solid product, the water, and the at least one reacted liquid product from the reacted feed; and in a second reaction, converting the at least one reacted liquid product into a mixture of hydrocarbon oils, fuel gas, and carbon.

25. The process of claim 24 wherein the first reaction takes place at a temperature between about 150° C. and about 330° C.

26. The process of claim 24 wherein the second reaction takes place at a temperature between about 300° C. and about 525° C.

27. The process of claim 24 wherein the first reaction takes place at about 250° C.

28. The process of claim 24 wherein the first reaction takes place at a pressure of 20-120 atmospheres.

29. The process of claim 24 wherein the first reaction takes place at a pressure of about 50 atmospheres.

30. The process of claim 24 wherein said one or more reagents is sodium.

31. The process of claim 24 wherein said one or more reagents is sulfur.

32. The process of claim 24 wherein said one or more reagents creates reducing conditions appropriate for liberation of ammonia.

33. The process of claim 24 wherein said one or more reagents creates $H_2SO_4$ in situ.

* * * * *